(12) United States Patent
Gilligan et al.

(10) Patent No.: US 6,960,583 B2
(45) Date of Patent: Nov. 1, 2005

(54) PYRAZOLOTRIAZINES AS CRF ANTAGONISTS

(75) Inventors: Paul J. Gilligan, Wilmington, DE (US); Richard G. Wilde, Newark, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/803,415

(22) Filed: Mar. 18, 2004

(65) Prior Publication Data

US 2004/0176376 A1 Sep. 9, 2004

Related U.S. Application Data

(62) Division of application No. 09/990,138, filed on Nov. 21, 2001, which is a continuation of application No. 09/543,290, filed on Apr. 5, 2000, now abandoned.

(60) Provisional application No. 60/128,008, filed on Apr. 6, 1999.

(51) Int. Cl.[7] ..................... C07D 487/04; A61K 31/53; A61P 3/04; A61P 25/22; A61P 25/24
(52) U.S. Cl. ........................................ 514/243; 544/184
(58) Field of Search ........................... 544/184; 514/243

(56) References Cited

U.S. PATENT DOCUMENTS

| | | |
|---|---|---|
| 3,910,907 A | 10/1975 | O'Brien, et al. |
| 3,920,652 A | 11/1975 | Springer et al. |
| 3,995,039 A | 11/1976 | Rooney et al. |
| 4,021,556 A | 5/1977 | Springer et al. |
| 4,567,263 A | 1/1986 | Eicken et al. |
| 4,621,556 A | 11/1986 | Soltysiak et al. |
| 4,892,576 A | 1/1990 | Kruger et al. |
| 4,997,940 A | 3/1991 | Vinogradoff et al. |
| 5,137,887 A | 8/1992 | Hashimoto et al. |
| 5,397,774 A | 3/1995 | Nugent et al. |
| 5,484,760 A | 1/1996 | Bussler et al. |
| 6,060,478 A | 5/2000 | Gilligan et al. .............. 514/258 |
| 6,124,289 A | 9/2000 | He et al. ..................... 514/245 |
| 6,136,809 A | 10/2000 | Gilligan et al. .............. 514/258 |
| 6,191,131 B1 | 2/2001 | He et al. ..................... 514/246 |
| 6,194,410 B1 | 2/2001 | Bos et al. .................... 514/246 |

FOREIGN PATENT DOCUMENTS

| | | |
|---|---|---|
| DE | 4 243 279 | 6/1994 |
| EP | 0 374 448 | 6/1990 |
| EP | 0 511 528 | 2/1994 |
| EP | 0 549 149 | 4/1994 |
| EP | 0 594 149 A3 | 4/1994 |
| EP | 0 662 477 | 7/1995 |
| EP | 0 269 859 | 10/1995 |
| EP | 0 714 898 | 6/1996 |
| EP | 0 521 622 | 8/1997 |
| EP | 0 591 528 | 12/1998 |
| EP | 0 531 901 | 3/2003 |
| WO | WO 92/10098 | 6/1992 |
| WO | WO 94/09017 | 4/1994 |
| WO | WO 95/10506 | 4/1995 |
| WO | WO 95/35298 | 12/1995 |
| WO | WO 97/29109 | 8/1997 |
| WO | WO 98/03510 | 1/1998 |
| WO | WO 98/08847 | 3/1998 |
| WO | WO 99/01454 | 1/1999 |
| WO | WO 99/38868 A | 8/1999 |

OTHER PUBLICATIONS

Gray et al. Journal of chemical society, Perkins transactions I: Organic and Bio–Organic Chemistry 8, 885–888, 1978.*
Mitchell, Neurosci. Biobehav. Rev. 22(5); 635–651, 1998.*
Deeb, A., et .al, "Preparation of naphtha[2,1–e]pyrazolo[5,1–c][1,2,4]triazine, dipyrazolo[5,1–c:3′,4′–e][1,2,4]triazines and pyrazolo–[1,5–c][1,2,4]triazine derivatives,"Collect. Czech. Chem. Commun, 1990, 55, 2790–2794.
Ege, G., et al. "Reactions with diazoazoles. Part IV. (1). [7+2]–and [11+2]–cyclocondensation reactions of diazoazoles with acyltriphenylphosphonium methylides to azolo [5,1cII1,2,4]triazines," J. Heterocyclic Chemistry, Jun. 1981, 18(4), 675–677.
Gray, E.J., et al., "Triazines and related products. Part 21. Cyclisation of 3–amino–5–hydrazinopyrazole and 3–amino–5–hydrazino–1,2,4–triazole to azolo–[5,1–c][1,2,4]triazines," J. Chemical Society, 1978, 885–888.
Ibrahim, et al., Arch. Pharm. (Weinheim), 1987, 320, 487–491.
Journal of Med. Chem., 1981, 24, 610–613.
Joshi, et al., J. Prakt. Chemie, 1979, 321(2), 341–344.
Kandeel, E.M., et al., "Reactions with heterocyclic amidines . . . ," Chemical Astracts Service, Columbus, OH, Accession No. 99:122411, RN87031–23–0 & Arch. Pharm. (Weinheim, Ger.), 1983, 316(8), 713–718.
Maquestiau, et al., Bull. Soc. Belg., 1992, 101(2), 131–136.
Ramiz, M.M.M., et al., "Studies on amino–azoles; synthesis of . . . ," Chemical Abstracts Service, Columbus, OH, Accession No. 112:35748, RN124612–21–1 & Arch. Pharm. (Weinheim, Ger.), 1989, 322(9), 557–560.
Senga, K., et al., "Synthesis and enzymic activity of various substituted pyrazolo[1 5–a]–1,3,5–triazines as adenosine cyclic 3′,5′–phosphate phosphodiesterase inhibitors," J. Med. Chem., 1982, 25, 243–249.

(Continued)

Primary Examiner—Venkataraman Balasubramanian
(74) Attorney, Agent, or Firm—Shah R. Makujina; Woodcock Washburn, LLP

(57) ABSTRACT

The present invention relates to pyrazolotriazines according to formula (I)

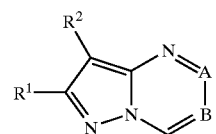

and stereoisomers, isomers and salts thereof wherein $R^1$–$R^5$ are selected from certain alkyl, aryl and heteroaryl species as defined in the specification wherein all of the compounds are useful as CRF antagonists and are thus useful in the treatment of neurological disorders as well as a multitude of other CRF associated diseases or conditions.

8 Claims, No Drawings

OTHER PUBLICATIONS

Springer, et al., *J. Med. Chem.,* 1976, 19(2), 291–296.

Strohmeyer, T.W., et al., "New synthesis of 2,4–dialkyl . . . ," *J. Het. Chem.,* 1985, 22(7), 7–10.

*J. Het. Chem.,* 1985, 22, 610.

Arató, M., et al., "Elevated CSF CRF in suicide victims," *Biol. Psychiatry,* 1989, 25, 355–359.

Armarego, W.L.F., Purification of Laboratory Chemicals, 3rd Ed. *Pergamon Press, NY,* 1988.

Banki, C.M., et al., "CSF corticotrophin–releasing factor–like immunoreactivity in depression and schizophrenia," *Am. J. Psychiatry,* 1987, 144(7), 873–877.

Battaglia, G., et al., "Characterization of corticotropin–releasing factor receptor–mediated adenylate cyclase activity in the rat central nervous system," *Synapse,* 1987, 1, 572–581.

Berridge, C.W., et al., "A corticotrophin–releasing factor antagonist reverses the stress–induced changes of exploratory behavior in mice," *Horm. And Behav.,* 1987, 21, 393–401.

Berridge, C.W., et al., "Corticotropin–releasing factor elicits naloxone sensitive stress–like alterations in exploratory behavior in mice," *Regulator Peptides,* 1986, 16, 83–93.

Blalock, J.E., "A molecular basis for bidirectional communication between the immune and neuroendocrine sysems," *Physiological Reviews,* 1989, 69(1), 1–32.

Britton, D.R., et al., "Intraventricular corticotrophin–releasing factor enhances behavioral effects of novelty," *Life Sci.,* 1982, 31, 363–367.

Britton, K.T., et al., "Corticotropin releasing factor and amphetamine exaggerate partial agonist properties of benzodiazepine antagonist Ro 15–1788 in the conflict test," *Psychopharmacology,* 1988, 94, 306–311.

Britton, K.T., et al., "Chlordiazepoxide attenuates response suppression induced by corticotrophin–releasing factor in the conflict test," *Psychopharmacology,* 1985, 86, 170–174.

DeSouza, E.B., "CRH defects in alzheimer's and other neurologic diseases," *Hosp. Practice,* 1988, 23, 59–71.

DeSouza, E.B., "Corticotropin–releasing factor receptors in the rat central nervous system: characterization and regional distribution," *J. Neurosci.,* 1987, 7(1), 88–100.

DeSouza, E.B., et al., "Corticotropin–releasing factor receptors are widely distributed within the rat central nervous system: an autoradiographic study," *J. Neurosci.,* 1985, 5(12), 3189–3203.

Dunn, A.J., et al., "Physiological and behavioral responses to corticotrophin–releasing factor administration: is CRF a mediator of anxiety or stress responses?, " *Brain Res. Rev.,* 1990, 15, 71–100.

France, R.D., et al., "CSF corticotrophin–releasing factor–like immunoactivity in chronic pain patients with and without major depression," *Biol. Psychiatry,* 1988, 23, 86–88.

Gold, P.W., et al., "Psychiatric implications of basic and clinical studies with corticotrophin–releasing factor," *Am. J. Psychiatry,* 1984, 141(5), 619–627.

Gold, P.W., et al., "Responses to corticotrophin–releasing hormone in the hypercortisolism of depression and cushing's disease," *New Eng. J. Med.,* 1986, 314, 1329–1335.

Grigoriadis, D.E., et al., "Effects of chronic antidepressant and benzodiazepine treatment on corticotrophin–releasing–factor receptors in rat brain and pituitary," *Neuropsychopharmacology,* 1989, 2(1), 53–60.

Holsboer, F., et al., "Acth and multisteroid responses to corticotrophin–releasing factor in depressive illness: relationship to multisteroid responses after acth stimulation and dexamethasone suppression," *Psychoneuroendocrinology,* 1984, 9(2), 147–160.

Koob, G.F., "Stress, corticotrophin–releasing factor, and behavior," *Persp. Behav. Med.,* 1985, 2, 39–52.

Lancelot, J.–C., et al., "Pyrazolo[1,5d]triazines–1,2,4. I. Dérivépyrazoliques," *J. Het. Chem.,* 1981, 1319–1324.

Morley, J.E., "Minireview neuropeptides: conductors of the immune orchestra," *Life Sci.,* 1987, 41, 527–544.

Lee, J.J., et al., "Synthesis of aryl ω–(1–methyl–5–imidazolyl and 1H–5–tetrazolyl)alkyl ketones [1]," *J. Het. Chem.,* 1998, 35, 81–87.

Munson, et al., "Ligand: A versatile computerized approach for characterization of ligand–binding systems," *Anal. Biochem.,* 1980, 107, 220–239.

Nemeroff, C.B., et al., "Reduced corticotrophin releasing factor binding sites in the frontal cortex of suicide victims," *Arch. Gen. Psychiatry,* 1988, 45, 577–579.

Nemeroff, C.B., et al., "Elevated concentrations of CSF corticotrophin–releasing factor–like immunoreactivity in depressed patients," *Science,* 1984, 226, 1342–1344.

Remington's Pharmaceutical Sciences, 17th Ed., *Mack Publishing Co., Easton, PA,* 1985, p. 1418.

River, J., et al., "Characterization of rat hypothalamic corticotrophin–releasing factor," *Proc. Nat. Acad. Sci. USA,* 1983, 80, 4851–4855.

Sapolsky, R.M., "Hypercortisolism among socially subordinate wild baboons originates at the CNS level," *Arch. Gen. Psychiatry,* 1989, 46, 1047–1051.

Swerdlow, N.R., et al., "Corticotropin–releasing factor potentiates acoustic startle in rats: blockage by chlordiazepoxide," *Psychopharmacology,* 1986, 88, 147–152.

Vale, W., et al., "Characterization of a 41–residue ovine hypothalamic peptide that stimulates secretion of corticotrophin and β–endorphin," *Science,* 1981, 213, 1394–1397.

Vale, W., et al., "Chemical and biological characterization of corticotrophin releasing factor," *Rec. Prog. Horm. Res.,* 1983, 39, 245–270.

Valentino, R.J., et al., "Effects of CRF on spontaneous and sensory–evoked activity of locus coeruleus neurons," in "Corticotropin–Releasing Factor: Basic And Clinical Studies Of A Neuropeptide," De Souza, E.B., et al. (Eds.), *CRC Press,* 1990, 217–231.

\* cited by examiner

PYRAZOLOTRIAZINES AS CRF ANTAGONISTS

CROSS-REFERENCE TO RELATED APPLICATIONS

This application is a divisional of U.S. application Ser. No. 09/990,138, filed Nov. 21, 2001, now allowed, which is a continuation of U.S. application Ser. No. 09/543,290, filed Apr. 5, 2000, now abandoned, which in turn claims priority of U.S. Provisional Application No. 60/128,008, filed Apr. 6, 1999. The disclosures of these prior applications are incorporated herein by reference in their entireties.

FIELD OF THE INVENTION

The present invention relates to novel compounds, compositions, and methods for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. In particular, the present invention relates to novel pyrazolotriazines, pharmaceutical compositions containing such compounds and their use in treating psychiatric disorders, neurological diseases, immunological, cardiovascular or heart-related diseases and colonic hypersensitivity associated with psychopathological disturbance and stress.

BACKGROUND OF THE INVENTION

Corticotropin releasing factor (herein referred to as CRF), a 41 amino acid peptide, is the primary physiological regulator of proopiomelanocortin (POMC)—derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

It has been further postulated that CRF has a role in immunological, cardiovascular or heart-related diseases such as hypertension, tachycardia and congestive heart failure, stroke, osteoporosis, premature birth, psychosocial dwarfism, stress-induced fever, ulcer, diarrhea, postoperative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

DuPont Merck PCT application US94/11050 describes corticotropin releasing factor antagonist compounds of the formula:

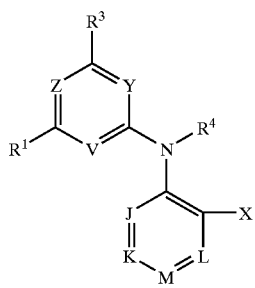

and their use to treat psychiatric disorders and neurological diseases. Included in the description are fused pyridines and pyrimidines of the formula:

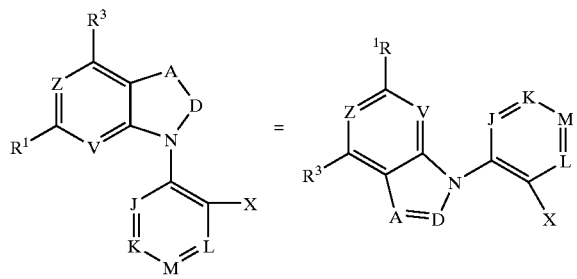

where: V is $CR^{1a}$ or N; Z is $CR^2$ or N; A is $CR^30$ or N; and D is $CR^{28}$ or N.

WO 98/03510, published in January, 1998, also describes a series of CRF antagonist compounds having the formula:

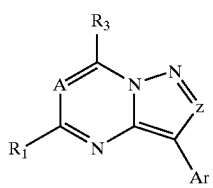

wherein z is N or $CR^2$ and A is N or CR.

WO 97/29109, published in August, 1997, similarly describes certain CRF antagonist compounds having the formula:

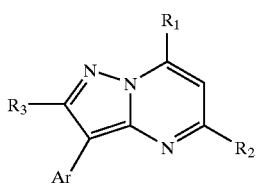

wherein Ar is phenyl, pyridyl and substituted versions thereof.

WO 98/08847, published Mar. 5, 1998, discloses CRF antagonist compounds of the formula:

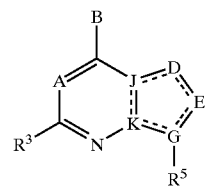

wherein B is selected from a variety of non-aryl groups and $R^5$ is selected from certain groups such as phenyl or pyridyl or substituted versions thereof.

WO 99/01454, published on Jan. 14, 1999, discloses CRF antagonist compounds of the formula:

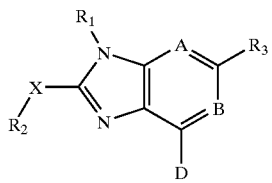

wherein D is an aryl or heteroaryl group and $R^1$ is selected from certain non-aryl or non-heteroaryl groups.

EP 0 269 859 (Ostuka, 1988) discloses pyrazolotriazine compounds of the formula

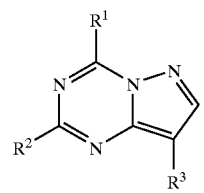

where $R^1$ is OH or alkanoyl, $R^2$ is H, OH, or SH, and $R^3$ is an unsaturated heterocyclic group, naphthyl or substituted phenyl, and states that the compounds have xanthine oxidase inhibitory activity and are useful for treatment of gout.

EP 0 594 149 (Ostuka, 1994) discloses pyrazolotriazine and pyrazolopyrimidine compounds of the formula

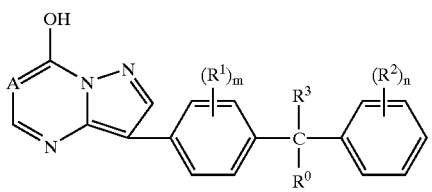

where A is CH or N, $R^0$ and $R^3$ are H or alkyl, and $R^1$ and $R^2$ are H, alkyl, alkoxyl, alkylthio, nitro, etc., and states that the compounds inhibit androgen and are useful in treatment of benign prostatic hypertrophy and prostatic carcinoma.

U.S. Pat. No. 3,910,907 (ICN Pharma, 1975) discloses pyrazolotriazines of the formula:

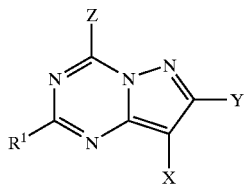

where R1 is $CH_3$, $C_2H_5$ or $C_6H_5$, X is H, $C_6H_5$, m-$CH_3C_6H_4$, CN, COOEt, Cl, I or Br, Y is H, $C_6H_5$, o-$CH_3C_6H_4$, or p-$CH_3C_6H_4$, and Z is OH, H, $CH_3$, $C_2H_5$, $C_6H_5$, n-$C_3H_7$, i-$C_3H_7$, SH, $SCH_3$, $NHC_4H_9$, or $N(C_2H_5)_2$, and states that the compounds are cAMP phosphodiesterase inhibitors useful as bronchodilators.

U.S. Pat. No. 3,995,039 discloses pyrazolotriazines of the formula:

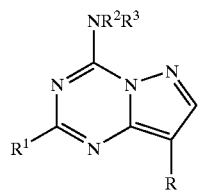

where $R^1$ is H or alkyl, $R^2$ is H or alkyl, $R^3$ is H, alkyl, alkanoyl, carbamoyl, or lower alkylcarbamoyl, and R is pyridyl, pyrimidinyl, or pyrazinyl, and states that the compounds are useful as bronchodilators.

U.S. Pat. No. 5,137,887 discloses pyrazolotriazines of the formula

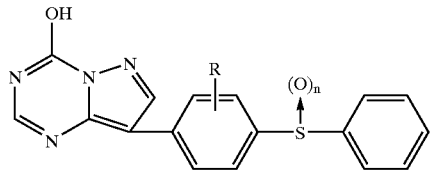

where R is lower alkoxy, and teaches that the compounds are xanthine oxidase inhibitors and are useful for treatment of gout.

U.S. Pat. No. 4,892,576 discloses pyrazolotriazines of the formula

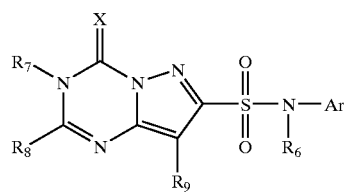

where X is O or S, Ar is a phenyl, naphthyl, pyridyl or thienyl group, $R_6$–$R_8$ are H, alkyl, etc., and $R_9$ is H, alkyl, phenyl, etc. The patent states that the compounds are useful as herbicides and plant growth regulants.

U.S. Pat. No. 5,484,760 and WO 92/10098 discloses herbicidal compositions containing, among other things, a herbicidal compound of the formula

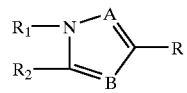

where A can be N, B can be $CR_3$, $R_3$ can be phenyl or substituted phenyl, etc., R is —$N(R_4)SO_2R_5$ or —$SO_2N(R_6)$ $R_7$ and $R_1$ and $R_2$ can be taken together to form

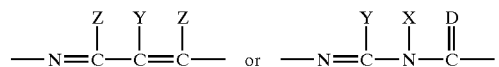

where X, Y and Z are H, alkyl, acyl, etc. and D is O or S.

U.S. Pat. No. 3,910,907 and Senga et al., J. Med. Chem., 1982, 25, 243–249, disclose triazolotriazines cAMP phosphodiesterase inhibitors of the formula

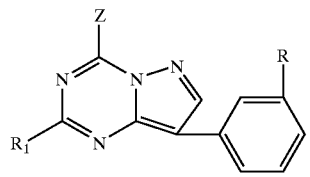

where Z is H, OH, $CH_3$, $C_2H_5$, $C_6H_5$, n-$C_3H_7$, iso-$C_3H_7$, SH, $SCH_3$, $NH(n-C_4H_9)$, or $N(C_2H_5)_2$, R is H or $CH_3$, and $R_1$ is $CH_3$ or $C_2H_5$. The reference lists eight therapeutic areas where inhibitors of cAMP phosphodiesterase could have utility: asthma, diabetes mellitus, female fertility control, male infertility, psoriasis, thrombosis, anxiety, and hypertension.

WO95/35298 (Otsuka, 1995) discloses pyrazolopyrimidines and states that they are useful as analgesics. The compounds are represented by the formula

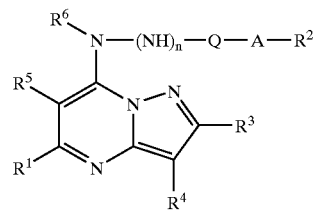

where Q is carbonyl or sulfonyl, n is 0 or 1, A is a single bond, alkylene or alkenylene, $R^1$ is H, alkyl, etc., $R^2$ is naphthyl, cycloalkyl, heteroaryl, substituted phenyl or phenoxy, $R^3$ is H, alkyl or phenyl, $R^4$ is H, alkyl, alkoxycarbonyl, phenylalkyl, optionally phenylthio-substituted phenyl, or halogen, $R^5$ and $R^6$ are H or alkyl.

EP 0 591 528 (Otsuka, 1991) discloses anti-inflammatory use of pyrazolopyrimidines represented by the formula

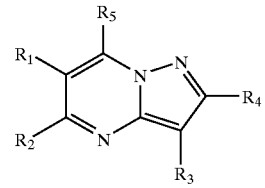

where $R_1$, $R_2$, $R_3$ and $R_4$ are H, carboxyl, alkoxycarbonyl, optionally substituted alkyl, cycloalkyl, or phenyl, $R_5$ is $SR_6$ or $NR_7R_8$, $R_6$ is pyridyl or optionally substituted phenyl, and $R_7$ and $R_8$ are H or optionally substituted phenyl.

Springer et al, J. Med. Chem., 1976, vol. 19, no. 2, 291–296 and Springer U.S. Pat. Nos. 4,021,556 and 3,920,652 disclose pyrazolopyrimidines of the formula

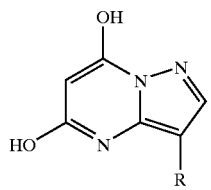

where R can be phenyl, substituted phenyl or pyridyl, and their use to treat gout, based on their ability to inhibit xanthine oxidase.

Joshi et al., J. Prakt. Chemie, 321, 2, 1979, 341–344, discloses compounds of the formula

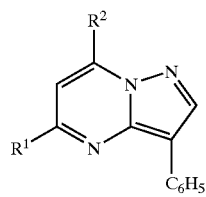

where $R^1$ is $CF_3$, $C_2F_5$, or $C_6H_4F$, and $R^2$ is $CH_3$, $C_2H_5$, $CF_3$, or $C_6H_4F$.

Maquestiau et al., Bull. Soc. Belg., vol. 101, no. 2, 1992, pages 131–136 discloses a pyrazolo[1,5-a]pyrimidine of the formula

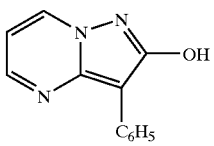

Ibrahim et al., Arch. Pharm. (weinheim) 320, 487–491 (1987) discloses pyrazolo[1,5-a]pyrimidines of the formula

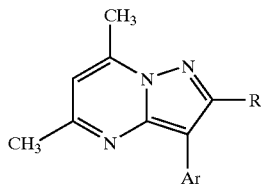

where R is NH2 or OH and Ar is 4-phenyl-3-cyano-2-aminopyrid-2-yl.

J. Med. Chem (1982), 25(3), 243–9 discloses compounds of the formula:

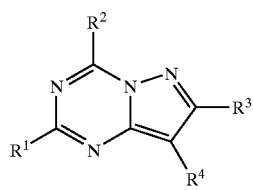

wherein $R^2$ is H, Ph, Pr, Sme, NHEt, NHBu, $Net_2$, piperidino, OH, NHPr, SH, $OCHMe_2$, Me, Set, Ome or Opr and $R^4$ is H, Br, $C_6H_4Me$-3, Ph, CN, $CO_2Et$ or Cl.

Other references which disclose azolopyrimidines include EP 0 511 528 (Otsuka, 1992), U.S. Pat. No. 4,997,940 (Dow, 1991), EP 0 374 448 (Nissan, 1990), U.S. Pat. No. 4,621,556 (ICN, 1997), EP 0 531 901 (Fujisawa, 1993), U.S. Pat. No. 4,567,263 (BASF, 1986), EP 0 662 477 (Isagro, 1995), DE 4 243 279 (Bayer, 1994), U.S. Pat. No. 5,397,774 (Upjohn, 1995), EP 0 521 622 (Upjohn, 1993), WO 94/09017 (Upjohn, 1994), J. Med. Chem., 24, 610–613 (1981), and J. Het. Chem., 22, 601 (1985) or others as additionally described herein.

SUMMARY OF THE INVENTION

In accordance with one aspect, the present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

According to another aspect, the present invention provides novel compounds of formula (I) (described below) which are useful as antagonists of the corticotropin releasing factor and which include pyrazolo[1,5-a][1,3,5]triazines and pyrazolo[1,5-a][1,2,4]triazines. The compounds of the present invention exhibit activity as corticotropin releasing factor antagonists and appear to suppress CRF hypersecretion. The present invention also includes pharmaceutical compositions containing such compounds of formula (I), and methods of using such compounds for the suppression of CRF hypersecretion, and/or for the treatment of anxiogenic disorders.

According to yet another aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma;

ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in mammals. The preferred uses include treatment of depression and anxiety.

The invention further includes use of a compound of formula I with the variables as recited herein in therapy or the use of a compound of formula I in the manufacture of a medicament for the treatment of CRF related diseases or disorders, including anxiety and depression.

According to a still further aspect of the invention, the compounds provided by this invention (and especially labelled compounds of this invention) are also useful as standards and reagents in determining the ability of a potential pharmaceutical to bind to the CRF receptor.

DETAILED DESCRIPTION OF INVENTION

[1] Thus, in a first embodiment, the present invention provides a novel compound of formula I:

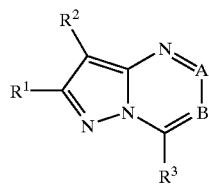

(I)

or a stereoisomer or pharmaceutically acceptable salt thereof, wherein:
A equals N or $CR^5$;
B equals N or $CR^4$;
provided that both A and B cannot be N or provided that A can not be $CR^5$ and B can not be $CR^4$ to form a pyrazolopyrimidine; and wherein,
$R^1$ is independently selected from the group consisting of
H,
halogen,
CN,
$C_{1-6}$ alkyl,
$C_{2-10}$ alkenyl,
$C_{2-10}$ alkynyl,
$C_{3-6}$ cycloalkyl,
$C_{1-6}$ alkyloxy,
$C_{1-6}$ alkyls(O)$_n$,
—$NR^{1a}R^{1B}$ wherein $R^{1a}$ and $R^{1b}$ are independently selected from H, $C_{1-4}$ alkyl, $C_{3-8}$ cycloalkyl, —C(O)$C_{1-4}$alkyl, $C_{1-6}$ alkyl$NR^{1a}R^{1b}$,
$NR^{1a}COR^{1b}$,
—C(O)$NR^{1a}R^{1b}$,
—O—C(O)$C_{1-4}$alkyl,
—$XR^{1c}$ wherein $R^{1c}$ is selected from H or —$C_{1-4}$ alkylaryl;

X is selected from 0 or S(O)$_n$,
wherein $R^1$ is substituted with 0–6 substituents selected from halogen, $C_{1-4}$ alkyl, $C_{3-8}$ cycloalkyl, $C_{1-6}$ alkyloxy, $C_{1-4}$ haloalkyl, $C_{1-4}$alkylamino, $C_{2-8}$dialkylamino, $C_{1-4}$alkyloxy, $C_{1-4}$ alkylthio, $C_{1-4}$ alkylsulfinyl or $C_{1-4}$ alkylsulfonyl;
$R^2$ is selected from the group consisting of
H, $OR_7$, SH, $NR^6R^7$, C(OH) $R^6$, $R^{6a}$, $C(OR^7)R^6R^{6a}$, $S(O)_n R^{13}$, $COR^7$, $CO_2R^7$, $CHR^6(OR^7)R^{6a}$, OC(O) $R^{13}$NO, $NO_2$, $NR^6C(O)R^7$, $N(COR^7)_2$, $NR^8CONR^6R^7$ or $NR^6CO_2R^7$; or $R^2$ is selected from:
$C_{1-10}$ alkyl,
$C_{2-10}$ alkenyl,
$C_{2-10}$ alkynyl,
$C_{3-8}$ cycloalkyl,
$C_{3-6}$ cycloalkyl $C_{1-6}$ alkyl,
$C_{1-10}$ alkyloxy,
$C_{1-10}$ alkyloxy$C_{1-10}$ alkyl,
—$SO_2$—$C_{1-10}$alkyl
—$SO_2R^{2a}$ wherein $R^{2a}$ is aryl,
—$SO_2R^{2b}$ wherein $R^{2b}$ is heteroaryl,
—$NR^{2C}R^{2D}$ wherein $R^{2c}$ and $R^{2d}$ are independently selected from H, $C_{1-8}$ alkyl, $S(O)_n C_{1-4}$alkyl, $C(O)NR^{2c}R^{2d}$, $CO_2C_{1-4}$alkyl, $C_{3-8}$ cycloalkyl, $C_{1-6}$ alkyloxy$C_{1-6}$ alkyl, —$C(O)C_{1-4}$alkyl or $R^{2c}$ and $R^{2d}$ may join to form a heterocyclic ring having 0–3 heteroatoms selected from O, N or S,
-halogen,
—CN,
—C(O)-L wherein L is selected from H, $NR^{2c}R^{2d}$, $C_{1-6}$ alkyl or $OC_{1-4}$ alkyl, $O(CH_2)_m OR$ wherein R is $C_{1-3}$ alkyl, $O(CH_2)_m$—$NR^{2c}R^{2d}$, OH, $C(O)OC_{1-6}$alkyl, or aryl or heteroaryl wherein m is 1–4; or
—OC(O)-M wherein M is selected from $C_{1-4}$ alkyl, $C_{1-4}$ haloalkyl, $C_{2-8}$ alkoxyalkyl, $C_{3-6}$cycloalkyl, $C_{4-12}$ cycloalkylalkyl, aryl, $C_{1-6}$ alkylaryl, heteroaryl, $C_{1-6}$ alkylheteroaryl;
n is 0, 1 or 2; and wherein
$R^2$ is substituted with 0–3 substituents independently selected from R', R", R''' wherein R', R" and R''' are independently selected from $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{2-6}$ alkynyl, $C_{1-6}$ alkyloxy, hydroxy, or
$R^2$ is substituted with 0–3 substituents independently selected from:
halogen,
—CN,
—$S(O)_n R^{2e}$ wherein $R^{2e}$ is selected from $C_{1-4}$ alkyl, $C_{1-4}$ haloalkyl, $C_{1-4}$ alkyloxy $C_{1-4}$ alkyl, $C_{3-6}$ cycloalkyl;
—$COR^{2f}$ wherein $R^{2f}$ is selected from H, $C_{1-4}$ alkyl, $C_{1-4}$ haloalkyl, $C_{1-4}$ alkyloxy $C_{1-4}$ alkyl, $C_{3-6}$ cycloalkyl, and $C_{3-6}$ cycloalkyl$C_{1-4}$ alkyl;
—$CO_2R^{2f}$,
—$NR^{2g}COR^{2f}$ wherein $R^{2g}$ is selected from H, $C_{1-6}$ alkyl, $C_{3-7}$ cycloalkyl, $C_{3-6}$ cycloalkyl $C_{1-6}$ alkyl;
—$N(COR^{2f})_2$,
—$NR^{2g}CONR^{2f}R^{2h}$, wherein $R^{2h}$ is selected from H, $C_{1-6}$ alkyl, $C_{1-4}$ haloalkyl, $C_{1-4}$ alkoxy $C_{1-4}$ alkyl, $C_{3-6}$ cycloalkyl and $C_{3-6}$ cycloalkyl$C_{1-6}$ alkyl;
—$NR^{2g}CO_2R^{2e}$,
—$CONR^{2g}R^{2h}$,
1-morpholinyl,
1-piperidinyl,
1-piperazinyl,
and
$C_{3-8}$ cycloalkyl wherein 0–1 carbon atoms in the $C_{4-8}$ cycloalkyl is replaced by a group selected from —O—, —S(O)$_n$—, —NR$^{2g}$—, —NCO$_2$R$^{2e}$, —NCOR$^{2e}$, and —NSO$_2$R$^{2e}$; and wherein N$_4$ in 1-piperazinyl is substituted with 0–1 substituents selected from R$^{2g}$, CO$_2$R$^{2e}$, COR$^{2e}$ and SO$_2$R$^{2e}$; or the group R$^{2i}$, R$^{2j}$, R$^{2k}$, C$_{1-6}$ alkyl, C$_{2-8}$ alkenyl, C$_{2-8}$ alkynyl, Br, Cl, F, I, C$_{1-4}$ haloalkyl, —OR$^{2g}$, —NR$^{2g}$R$^{2h}$, —C$_{1-6}$ alkyl-OR$^{2g}$, and C$_{3-8}$ cycloalkyl which is substituted with 0–1 R$^{21}$ and in which 0–1 carbons of C$_{4-8}$ cycloalkyl is replaced by —O—, wherein R$^{2i}$ is selected from aryl wherein aryl includes phenyl, naphthyl, indanyl and indenyl, each R$^{2i}$ being substituted with 0–1 OR$^{2m}$ and 0–5 substituents independently selected from the group C$_{1-6}$ alkyl, C$_{3-6}$ cycloalkyl, Br, Cl, F, I, C$_{1-4}$ haloalkyl, —CN, nitro, —SH, —S(O)$_n$R$^{2n}$, —COR$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2n}$, —NR$^{2o}$R$^{2p}$ and —CONR$^{2o}$R$^{2p}$;

R$^{2j}$ is selected from heteroaryl wherein heteroaryl includes pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;

R$^{2k}$ is heterocyclyl which is a saturated or partially saturated heteroaryl as defined for R$^{2j}$, each heterocyclyl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CON R$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;

wherein

R$^{21}$ is H, C$_{1-4}$ alkyl, C$_{3-6}$ cycloalky-C$_{1-4}$ alkyl and C$_{3-8}$ cycloalkyl;

R$^{2m}$ is H, C$_{1-6}$ alkyl, C$_{3-6}$ cycloalkyl C$_{1-6}$ alkyl, C$_{1-2}$ alkyloxy C$_{1-2}$ alkyl, C$_{1-4}$ haloalkyl, R$^{2q}$S(O)$_n$—C$_{1-4}$ alkyl and R$^{2r}$R$^{2s}$N—C$_{2-4}$ alkyl;

R$^{2n}$ is H, C$_{1-6}$ alkyl, C$_{3-10}$ cycloalkyl, C$_{3-6}$ cycloalkyl-C$_{1-6}$ alkyl, C$_{1-2}$ alkyloxy C$_{1-2}$ alkyl, and C$_{1-4}$ haloalkyl;

R$^{2o}$ and R$^{2p}$ are independently selected at each occurrence from H, C$_{1-6}$ alkyl, C$_{3-10}$ cycloalkyl, C$_{3-6}$ cycloalkyl C$_{1-6}$ alkyl and C$_{1-4}$ haloalkyl;

R$^{2q}$ is selected from C$_{1-6}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl(C$_{1-4}$ alkyl), heteroaryl and heteroaryl (C$_{1-4}$ alkyl)- and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy C$_{1-4}$ haloalkoxy, and dimethylamino;

R$^{2r}$R$^{2s}$ taken together with the N form 1-pyrrolidinyl, 1-morpholinyl, 1-piperidinyl or 1-piperazinyl wherein N$_4$ in 1-piperazinyl is substituted with 0–1 substituents selected from the group R$^{2t}$, CO$_2$R$^{2q}$, COR$^{2q}$ and SO$_2$R$^{2q}$, R$^{2t}$ is selected from H, C$_{1-4}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl (C$_{1-4}$ alkyl)-, heteroaryl and heteroaryl (C$_{1-4}$ alkyl);

R$^3$ is selected from an aryl or heteroaryl group attached through an unsaturated carbon atom;

aryl is selected from phenyl, naphthyl, indanyl and indenyl, each aryl being substituted with 0–5 substituents independently selected at each occurrence from C$_{1-6}$ alkyl, C$_{3-6}$ cycloalkyl, methylenedioxy, C$_{1-4}$ alkyloxy-C$_{1-4}$ alkyloxy, —OR$^{2m}$, Br, Cl, F, I, C$_{1-4}$ haloalkyl, —CN, —NO$_2$, —SH, —S(O)$_n$R$^{2n}$, —COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and CONR$^{2o}$R$^{2p}$;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substituted at 0–4 carbon atoms with a substituent independently selected at each occurrence from the group C$_{1-6}$ alkyl, C$_{3-6}$ cycloalkyl, Br, F, I, C$_{1-4}$ haloalkyl, —CN, NR$^{2g}$R$^{2h}$, nitro, —OR$^{2m}$, —SH, —S(O)$_n$R$^{2n}$, COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$ and each heteroaryl being substituted at any nitrogen atom with 0–1 substituents selected from the group R$^{2g}$, CO$_2$R$^{3a}$, COR$^{3a}$ and SO$_2$R$^{3a}$ wherein, R$^{3a}$ is selected from the group C$_{1-6}$ alkyl, C$_{1-4}$ cycloalkyl-C$_{1-6}$ alkyl and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy, C$_{1-4}$ haloalkoxy, and dimethylamino;

R$^4$ and R$^5$ are independently selected at each occurrence from H, Br, Cl, F, I, —CN, C$_{1-6}$ alkyl, C$_{2-6}$ alkenyl, C$_{2-6}$ alkynyl, C$_{3-8}$ cycloalkyl, C$_{1-6}$ alkyloxy, C$_{1-6}$ alkylthio, C$_{1-6}$ alkylsulfinyl, C$_{1-6}$ alkylsulfonyl, amino, C$_{1-4}$ alkylamino, (C$_{1-4}$ alkyl)$_2$ amino and phenyl, each phenyl is substituted with 0–3 groups selected from the group consisting of C$_{1-7}$ alkyl, C$_{3-8}$ cycloalkyl, Br, Cl, F, I, —C(O)H, C$_{1-4}$ haloalkyl, nitro, C$_{1-4}$ alkoxy, C$_{1-4}$ haloalkoxy, C$_{1-4}$ alkylthio, C$_{1-4}$ alkylsulfinyl, C$_{1-4}$ alkylsulfonyl, C$_{1-6}$ alkylamino and (C$_{1-4}$ alkyl)$_2$ amino and wherein R$^4$ and R$^5$ non-phenyl groups may be substituted with 0–5 substituents selected from OH, halogen, —C(O)H, —OC$_{1-6}$-alkyl and C$_{1-6}$ haloalkyl, C$_{1-6}$ alkyl, C$_{3-7}$ c-alkyl, C$_{1-6}$ alkyl(OH)$_n$CO$_2$R wherein R is H or C$_{1-6}$ alkyl, C$_{1-6}$ alkyl(OH)$_n$, wherein n is 0–3 or R$^4$ and R$^5$ may join together to form a C$_{3-6}$ alkylene chain;

R$^6$, R$^{6a}$ and R$^7$ are independently selected from: H, C$_{1-10}$ alkyl, C$_{3-10}$ cycloalkyl, C$_{3-10}$ alkenyl, C$_{3-10}$ alkynyl, C$_{1-10}$ haloalkyl, C$_{2-8}$ alkoxyalkyl, C$_{4-12}$ cycloalkylalkyl, C$_{5-10}$ cycloalkenyl, C$_{6-14}$ cycloalkenylalkyl;

R$^6$, R$^{6a}$ and R$^7$ are substituted with 0–6 substituents independently selected from halogen, C$_{1-4}$ alkyl, C$_{3-8}$ cycloalkyl, C$_{1-6}$ alkyloxy, C$_{1-4}$ haloalkyl;

with the proviso that the compounds of Formula I with R$^1$, R$^2$, R$^3$, R$^4$ and R$^5$ as specifically defined below are excluded:

(a) a compound of formula I wherein A=CR$^5$ with R$^5$ o-hydroxyphenyl, B=N, R$^3$=o-hydroxyphenyl, R$^1$=SMe and R$^2$=CN (Registry Reference 23/IS98062) and (b) a compound of formula I wherein A=CR$^5$, R$^5$=CH$_3$, B=N, R$^1$=Ph, R$^2$=Br and R$^3$ is Ph;
(c) a compound of formula I wherein A=CR$^5$, R$^5$=p-Cl-phenyl, B=N, R$^1$=Me, R$^2$=H and R$^3$=p-CF$_3$-phenyl (Registry reference 152/IS98062);
(d) a compound of formula I wherein A=CR$^5$, R$^5$=phenyl, B=N, R$^1$=Me, R$^2$=H and R$^3$=p-CF$_3$-phenyl(Registry reference 153/IS98062);
(e) a compound of formula I wherein A=CR$^5$, R$^5$=ethyl, B=N, R$^1$=Me, R$^2$=H and R$^3$=N-methyl-piperiazin-N-yl (registry reference 184/IS98062);
(f) a compound of formula I wherein A=CR$^5$, R$^5$ is p-Cl—Ph, R$^1$=H, R$^2$=H and R$^3$=p-CF$_3$—Ph (Registry reference 9/IS98179);
(g) a compound of formula I wherein A=CR$^5$, R$^5$=p-Cl—Ph, R$^1$=CH$_3$, R$^3$=H, R$^3$=p-CF$_3$—Ph (Registry reference 10/IS98179);
(h) a compound of formula I wherein A=CR$^5$, R$^5$=Ph, R$^1$=Me, R$^2$=H, R$^3$=p-CF$_3$—Ph (Registry reference 11/IS98179);
(i) a compound of formula I wherein A=CR$^5$, R$^5$=Ph, R$^1$=H, R$^2$=H, R$^3$=p-CF$_3$—Ph (Registry reference 12/IS98179);
(j) a compound of formula I wherein A=CR$^5$, R$^3$=Ph and R$^2$ is H, Br, CN, CO$_2$Et or Cl (J. Med. Chem. (1982), 25(3), 243–9;
(k) a compound of formula I wherein A=CR$^5$, R$^5$=CH$_3$, C$_2$H$_5$ or Ph, R$^1$=H, R$^2$=H and R$^3$=Ph (U.S. Pat. No. 3,910,907).

[1'] The present invention preferrably relates to a novel compound of formula I:

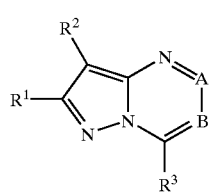

(I)

or a stereoisomer or pharmaceutically acceptable salt thereof, wherein:
A equals N or CR$^5$;
B equals N or CR$^4$;
provided that both A and B cannot be N or provided that A can not be CR$^5$ and B can not be CR$^4$ to form a pyrazolopyrimidine; and wherein,
R$^1$ is independently selected from the group consisting of
H,
halogen,
CN,
C$_{1-6}$ alkyl,
C$_{2-10}$ alkenyl,
C$_{2-10}$ alkynyl,
C$_{3-6}$ cycloalkyl,
C$_{1-6}$ alkyloxy,
C$_{1-6}$ alkyls (O)$_n$,
—NR$^{1a}$R$^{1B}$ wherein R$^{1a}$ and R$^{1b}$ are independently selected from H, C$_{1-4}$ alkyl, C$_{3-8}$ cycloalkyl, —C(O)C$_{1-4}$alkyl,
C$_{1-6}$ alkylNR$^{1a}$R$^{1b}$,
NR$^{1a}$COR$^{1b}$,
—C(O)NR$^{1a}$R$^{1b}$,
—O—C(O)C$_{1-4}$alkyl,
—XR$^{1c}$ wherein R$^{1c}$ is selected from H or —C$_{1-4}$ alkylaryl;
X is selected from 0 or S(O)$_n$,
wherein R$^1$ is substituted with 0–6 substituents selected from halogen, C$_{1-4}$ alkyl, C$_{3-8}$ cycloalkyl, C$_{1-6}$ alkyloxy, C$_{1-4}$ haloalkyl, C$_{1-4}$alkylamino, C$_{2-8}$dialkylamino, C$_{1-4}$alkyloxy, C$_{1-4}$ alkylthio, C$_{1-4}$ alkylsulfinyl or C$_{1-4}$ alkylsulfonyl;

R$^2$ is selected from the group consisting of OR$^7$, SH, NR$^6$R$^7$, C(OH)R$^6$R$^{6a}$, C(OR$^7$)R$^6$R$^{6a}$, S(O)$_n$R$^{13}$, COR$^7$, CO$_2$R$^7$, CHR$^6$(OR$^7$)R$^{6a}$, OC(O)R$^{13}$, NO, NO$_2$, NR$^6$C(O)R$^7$, N(COR$^7$)$_2$, NR$^8$CONR$^6$R$^7$ or NR$^6$CO$_2$R$^7$; or R$^2$ is selected from:
C$_{1-10}$ alkyl,
C$_{2-10}$ alkenyl,
C$_{2-10}$ alkynyl,
C$_{3-8}$ cycloalkyl,
C$_{3-6}$ cycloalkyl C$_{1-6}$ alkyl,
C$_{1-10}$ alkyloxy,
C$_{1-10}$ alkyloxyC$_{1-10}$ alkyl,
—SO$_2$—C$_{1-10}$alkyl
—SO$_2$R$^{2a}$ wherein R$^{2a}$ is aryl,
—SO$_2$R$^{2b}$ wherein R$^{2b}$ is heteroaryl,
—NR$^{2c}$R$^{2D}$ wherein R$^{2c}$ and R$^{2d}$ are independently selected from H, C$_{1-8}$ alkyl, S(O)$_n$C$_{1-4}$alkyl, C(O)NR$^{2c}$R$^{2d}$, CO$_2$C$_{1-4}$alkyl, C$_{3-8}$ cycloalkyl, C$_{1-6}$ alkyloxyC$_{1-6}$ alkyl, —C(O)C$_{1-4}$alkyl or R$^{2c}$ and R$^{2d}$ may join to form a heterocyclic ring having 0–3 heteroatoms selected from O, N or S,
—C(O)-L wherein L is selected from H, NR$^{2c}$R$^{2d}$, C$_{1-6}$ alkyl O(CH$_2$)$_m$OR wherein R is C$_{1-3}$ alkyl, O(CH$_2$)$_m$—NR$^{2c}$R$^{2d}$,OH, C(O)OC$_{1-6}$alkyl, or aryl or heteroaryl wherein m is 1–4; or
—OC(O)-M wherein M is selected from C$_{1-4}$ alkyl, C$_{1-4}$ haloalkyl, C$_{2-8}$ alkoxyalkyl, C$_{3-6}$cycloalkyl, C$_{4-12}$ cycloalkylalkyl, aryl, C$_{1-6}$ alkylaryl, heteroaryl, C$_{1-6}$ alkylheteroaryl;
n is 0, 1 or 2; and wherein
R$^2$ is substituted with 0–3 substituents independently selected from R', R", R"' wherein R', R" and R"' are independently selected from C$_{1-6}$ alkyl, C$_{3-7}$ cycloalkyl, hydroxyC$_{1-6}$ alkyl, C$_{1-6}$ alkyloxyC$_{1-6}$ alkyl, C$_{2-6}$ alkenyl, C$_{2-6}$ alkynyl, C$_{1-6}$ alkyloxy, hydroxy, or
R$^2$ is substituted with 0–3 substituents independently selected from:
halogen,
—CN,
—S(O)$_n$R$^{2e}$ wherein R$^{2e}$, is selected from C$_{1-4}$ alkyl, C$_{1-4}$ haloalkyl, C$_{1-4}$ alkyloxy C$_{1-4}$ alkyl, C$_{3-6}$ cycloalkyl;
—COR$^{2f}$ wherein R$^{2f}$ is selected from H, C$_{1-4}$ alkyl, C$_{1-4}$ haloalkyl, C$_{1-4}$ alkyloxy C$_{1-4}$ alkyl, C$_{3-6}$ cycloalkyl, and C$_{3-6}$ cycloalkylC$_{1-4}$ alkyl;
—CO$_2$R$^{2f}$,
—NR$^{2g}$COR$^{2f}$ wherein R$^{2g}$ is selected from H, C$_{1-6}$ alkyl, C$_{3-7}$ cycloalkyl, C$_{3-6}$ cycloalkyl C$_{1-6}$ alkyl;
—N(COR$^{2f}$)$_2$,
—NR$^{2g}$CONR$^{2f}$R$^{2h}$, wherein R$^{2h}$ is selected from H, C$_{1-6}$ alkyl, C$_{1-4}$ haloalkyl, C$_{1-4}$ alkoxy C$_{1-4}$ alkyl, C$_{3-6}$ cycloalkyl and C$_{3-6}$ cycloalkylC$_{1-6}$ alkyl;
—NR$^{2g}$CO$_2$R$^{2e}$,
—CONR$^{2g}$R$^{2h}$,
1-morpholinyl,
1-piperidinyl,
1-piperazinyl,
and
C$_{3-8}$ cycloalkyl wherein 0–1 carbon atoms in the C$_{4-8}$ cycloalkyl is replaced by a group selected from —O—, —S(O)$_n$—, —NR$^{2g}$—, —NCO$_2$R$^{2e}$, —NCOR$^{2e}$, and —NSO$_2$R$^{2e}$; and wherein N$_4$ in 1-piperazinyl is substituted with 0–1 substituents selected from R$^{2g}$, CO$_2$R$^{2e}$, COR$^{2e}$ and SO$_2$R$^{2e}$; or
the group R$^{2i}$, R$^{2j}$, R$^{2k}$, C$_{1-6}$ alkyl, C$_{2-8}$ alkenyl, C$_{2-8}$ alkynyl, Br, Cl, F, I, C$_{1-4}$ haloalkyl, —OR$^{2g}$, —NR$^{2g}$R$^{2h}$, —$C_{1-6}$ alkyl-$OR^{2g}$, and $C_{3-8}$ cycloalkyl which is substituted with 0–1 $R^{21}$ and in which 0–1 carbons of $C_{4-8}$ cycloalkyl is replaced by —O—, wherein $R^{2i}$ is selected from aryl wherein aryl includes phenyl, naphthyl, indanyl and indenyl, each $R^{2i}$ being substituted with 0–1 $OR^{2m}$ and 0–5 substituents independently selected from the group $C_{1-6}$ alkyl, $C_{3-6}$ cycloalkyl, Br, Cl, F, I, $C_{1-4}$ haloalkyl, —CN, nitro, —SH, —$S(O)_nR^{2n}$, —$COR^{2m}$, —$OC(O)R^{2n}$, —$NR^{2g}COR^{2m}$, —$N(COR^{2m})_2$, —$NR^{2g}CONR^{2o}R^{2p}$, —$NR^{2g}CO_2R^{2n}$, —$NR^{2o}R^{2p}$ and —$CONR^{2o}R^{2p}$;

$R^{2j}$ is selected from heteroaryl wherein heteroaryl includes pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group $C_{1-6}$ alkyl, $C_{3-6}$ cycloalkyl, Br, Cl, F, I, $C_{1-4}$ haloalkyl, —CN, nitro, $OR^{2m}$, —SH, —$S(O)_nR^{2h}$, —$COR^{2m}$, —$OC(O)R^{2h}$, —$NR^{2g}COR^{2m}$, —$N(COR^{2m})_2$, —$NR^{2g}CONR^{2o}R^{2p}$, —$NR^{2g}CO_2R^{2h}$, —$NR^{2o}R^{2p}$ and —$CONR^{2o}R^{2p}$ and each heteroaryl being substituted on any nitrogen atom with 0–1 substituents selected from the group $R^{2g}$, $CO_2R^{2e}$, $COR^{2e}$ and $SO_2R^{2e}$;

$R^{2k}$ is heterocyclyl which is a saturated or partially saturated heteroaryl as defined for $R^{2j}$, each heterocyclyl being substituted on 0–4 carbon atoms with a substituent independently selected from the group $C_{1-6}$ alkyl, $C_{3-6}$ cycloalkyl, Br, Cl, F, I, $C_{1-4}$ haloalkyl, —CN, nitro, —$OR^{2m}$, —SH, —$S(O)_nR^{2h}$, —$COR^{2m}$, —$OC(O)R^{2h}$, —$NR^{2g}COR^{2m}$, —$N(COR^{2m})_2$, —$NR^{2g}CONR^{2o}R^{2p}$, $NR^{2g}CO_2R^{2h}$, —$NR^{2o}R^{2p}$ and —$CONR^{2o}R^{2p}$ and each heterocyclyl being substituted on any nitrogen atom with 0–1 substituents selected from the group $R^{2f}$, $CO_2R^{2e}$, $COR^{2e}$ and $SO_2R^{2e}$;

wherein $R^{21}$ is H, $C_{1-4}$ alkyl, $C_{3-6}$ cycloalky-$C_{1-4}$ alkyl and $C_{3-8}$ cycloalkyl;

$R^{2m}$ is H, $C_{1-6}$ alkyl, $C_{3-6}$ cycloalkyl $C_{1-6}$ alkyl, $C_{1-2}$ alkyloxy $C_{1-2}$ alkyl, $C_{1-4}$ haloalkyl, $R^{2q}S(0)_n$—$C_{1-4}$ alkyl and $R^{2r}R^{2s}N$—$C_{2-4}$ alkyl;

$R^{2n}$ is H, $C_{1-6}$ alkyl, $C_{3-10}$ cycloalkyl, $C_{3-6}$ cycloalkyl-$C_{1-6}$ alkyl, $C_{1-2}$ alkyloxy $C_{1-2}$ alkyl, and $C_{1-4}$ haloalkyl;

$R^{2o}$ and $R^{2p}$ are independently selected at each occurrence from H, $C_{1-6}$ alkyl, $C_{3-10}$ cycloalkyl, $C_{3-6}$ cycloalkyl $C_{1-6}$ alkyl and $C_{1-4}$ haloalkyl;

$R^{2q}$ is selected from $C_{1-6}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl), heteroaryl and heteroaryl ($C_{1-4}$ alkyl)- and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{2r}R^{2s}$ taken together with the N form 1-pyrrolidinyl, 1-morpholinyl, 1-piperidinyl or 1-piperazinyl wherein $N_4$ in 1-piperiazinyl is substituted with 0–1 substituents selected from the group $R^{2t}$, $CO_2R^{2q}$, $COR^{2q}$ and $SO_2R^{2q}$;

$R^{2t}$ is selected from H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl ($C_{1-4}$ alkyl)-, heteroaryl and heteroaryl ($C_{1-4}$ alkyl);

$R^3$ is selected from an aryl or heteroaryl group attached through an unsaturated carbon atom;

aryl is selected from phenyl, naphthyl, indanyl and indenyl, each aryl being substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —$OR^{2m}$, Br, Cl, F, I, $C_{1-4}$ haloalkyl, —CN, —$NO_2$, —SH, —$S(O)_nR^{2n}$, —$COR^{2m}$, —$CO_2R^{2m}$, —$OC(O)R^n$, —$NR^{2g}COR^{2m}$, —$N(COR^{2m})_2$, —$NR^{2g}CONR^{2o}R^{2p}$, —$NR^{2g}CO_2R^{2h}$, —$NR^{2o}R^{2p}$ and $CONR^{2o}R^{2p}$;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substituted at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, $NR^{2g}R^{2h}$, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$ and each heteroaryl being substituted at any nitrogen atom with 0–1 substituents selected from the group $R^{2g}$, $CO_2R^{3a}$, $COR^{3a}$ and $SO_2R^{3a}$ wherein, $R^{3a}$ is selected from the group $C_{1-6}$ alkyl, $C_{1-4}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^4$ and $R_5$ are independently selected at each occurrence from H, Br, Cl, F, I, —CN, $C_{1-6}$ alkyl, $C_{2-6}$ alkenyl, $C_{2-6}$ alkynyl, $C_{3-8}$ cycloalkyl, $C_{1-6}$ alkyloxy, $C_{1-6}$ alkylthio, $C_{1-6}$ alkylsulfinyl, $C_{1-6}$ alkylsulfonyl, amino, $C_{1-4}$ alkylamino, $(C_{1-4}$ alkyl$)_2$ amino and phenyl, each phenyl is substituted with 0–3 groups selected from the group consisting of $C_{1-7}$ alkyl, $C_{3-8}$ cycloalkyl, Br, Cl, F, I, —C(O)H, $C_{1-4}$ haloalkyl, nitro, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-6}$ alkylamino and $(C_{1-4}$ alkyl$)_2$ amino and wherein $R^4$ and $R^5$ non-phenyl groups may be substituted with 0–5 substituents selected from OH, halogen, —C(O)H, —$OC_{1-6}$-alkyl and $C_{1-6}$ haloalkyl, $C_{1-6}$ alkyl, $C_{3-7}$ c-alkyl, $C_{1-6}$ alkyl(OH)$_n CO_2R$ wherein R is H or $C_{1-6}$ alkyl, $C_{1-6}$ alkyl(OH)$_n$, wherein n is 0–3 or $R^4$ and $R^5$ may join together to form a $C_{3-6}$ alkylene chain;

$R^6$, $R^{6a}$ and $R^7$ are independently selected from: H, $C_{1-10}$ alkyl, $C_{3-10}$ cycloalkyl, $C_{3-10}$ alkenyl, $C_{3-10}$ alkynyl, $C_{1-10}$ haloalkyl, $C_{2-8}$ alkoxyalkyl, $C_{4-12}$ cycloalkylalkyl, $C_{5-10}$ cycloalkenyl, $C_{6-14}$ cycloalkenylalkyl;

$R^6$, $R^{6a}$ and $R^7$ are substituted with 0–6 substituents independently selected from halogen, $C_{1-4}$ alkyl, $C_{3-8}$ cycloalkyl, $C_{1-6}$ alkyloxy, $C_{1-4}$ haloalkyl.

[2] The present invention also relates to compounds of formula (Ia) and (Ib) below with the variables as recited above in group [1] or [1′]:

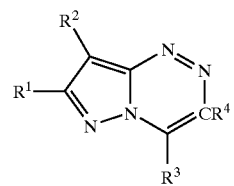

(Ia)

-continued

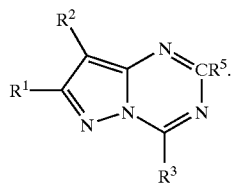
(Ib)

[3] The present invention relates to a compound as described directly above in [1], [1'] or [2] wherein
  $R^1$ is selected from $C_{1-6}$ alkyl, $C_{3-6}$ cycloalkyl, $C_{1-6}$ alkoxy, $C_{1-6}$ alkylthio, —$XR^{1c}$ wherein $R^1$ is substituted with 0–6 substituents selected from halogen, $C_{1-4}$ alkyl or $C_{1-4}$ haloalkyl;
  $R^2$ is selected from $C_{1-10}$ alkyl, $C_{2-10}$ alkenyl, $C_{2-10}$ alkynyl, $C_{3-8}$ cycloalkyl, $C_{3-6}$ cycloalkyl $C_{1-6}$ alkyl, —$NR^{2c}R^{2d}$ wherein $R^2$ is unsubstituted or substituted with 1–3 substitutents independently selected from the group $R^{2i}$, $R^{2j}$, $R^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$, —$NR^{2g}R^{2h}$, —$C_{1-6}$ alkyl$OR^{2g}$, and $C_{3-8}$ cycloalkyl which is substituted with 0–1 $R^{21}$ and in which 0–1 carbons of $C_{4-8}$ cycloalkyl is replaced by —O—.

[4] The present invention also relates to a compound described directly above in group [1] or [1'], [2] or [3] wherein $R^3$ is selected from an aryl group selected from phenyl or substituted versions thereof or a heteroaryl group selected from pyridyl or substituted versions thereof.

[5] The present invention relates to a compound described directly above in [1], [1'], [2], [3], or [4] wherein $R^3$ is substituted with 0–4 substituents independently selected from halogen, $C_{1-4}$ alkyloxy, $C_{1-6}$ alkyl or NR'R" wherein R' and R" are independently selected from H or $C_{1-6}$ alkyl.

[6] The present invention preferably relates to a compound as described directly above in groups [1], [1'], [2], [3], [4] or [5] wherein $R^3$ is selected from 2,4-dichlorophenyl, 2-chloro-4-methoxyphenyl, 2,4,6-trimethylphenyl, 2,4,6-trimethoxyphenyl, 2-dimethylamino-4-methyl-pyridin-5-yl, 2,4-dichloro-5-fluorophenyl, 2-chloro-4-methoxy-5-fluorophenyl, 2-methyl-4-methoxyphenyl, 2-methyl-4,6-dimethoxyphenyl, 2-chloro-4,5-dimethoxyphenyl or 2-chloro-4,6-dimethoxyphenyl.

[7] The present invention also preferably relates to a compound as described in the group [1], [1'], [2], [3], [4], [5], or [6] wherein $R^2$ is selected from $C_1$ alkyl of the formula —CR'R"R'" wherein R', R" and R"'40 are independently selected from H, $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{1-6}$ alkyloxy, hydroxy, with the proviso that each of R',R" and R'" cannot be H;
  or $R^2$ is selected from $NR^{2c}R^{2d}$ wherein $R^{2c}$ and $R^{2d}$ are independently selected from H or $C_{1-6}$ alkyl.

[8] The present invention preferably relates to a compound according to groups [1]–[7] and [1'] wherein $R^3$ is selected from an aryl or heteroaryl group attached through an unsaturated carbon atom wherein, aryl is phenyl, each phenyl being substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —$OR^{2m}$, Br, Cl, F, I, $C_{1-4}$ haloalkyl, —CN, —$NO_2$, —SH, —$S(O)_nR^{2n}$, —$COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$, —$NR^{2g}CO_2R^{2h}$, —$NR^{2o}R^{2p}$ and $CONR^{2o}R^{2p}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl and wherein, heteroaryl is selected at each occurrence from pyridyl, each pyridyl being substituted at 0–4 carbon atoms with a substituent independently selected at each occurrence from the group $C_{1-6}$ alkyl, $C_{3-6}$ cycloalkyl, Br, F, I, $C_{1-4}$ haloalkyl, —CN, nitro, —$OR^{2m}$, —SH, —$S(O)_nR^{2n}$, $COR^{2m}$, —$CO_2R^{2m}$, —$OC(O)R^{2n}$, —$NR^{2g}COR^{2m}$, —$N(COR^{2m})_2$, —$NR^{2g}CONR^{2o}R^{2p}$ and each pyridyl being substituted at any carbon atom with 0–1 substituents selected from the group $R^{2g}$, $CO_2R^{3a}$, $COR^{3a}$ and $SO_2R^{3a}$.

[9] The present invention preferably relates to a compound of formula (Ia)

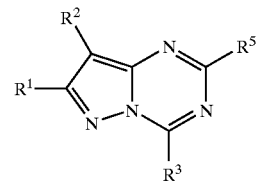

or a pharmaceutically acceptable salt thereof, wherein
  $R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_2$–$C_{10}$ cyanoalkyl, $C_3$–$C_6$cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;
  $R^2$ is selected from:
    —H, $OR^7$, SH, $S(O)_nR^{13}$, $COR^7$, $CO_2R^7$, $CHR^6(OR^7)$ $R^{6a}$, $OC(O)R^{13}$, $CH(OH)R^6$, $C(OH)R^6R^{6a}$, $C(OR^7)$ $R^6R^{6a}$, NO, $NO_2$, $NR^6COR^7$, $N(COR^7)_2$, $NR^8CONR^6R^7$, $NR^6CO_2R^7$, $NR^6R^7$, $NR^6S(O)_2R^7$, $N(S(O)_2R^7)_2$, $N(OR^7)R^6$ or $CONR^6R^7$;
  or
    —$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;
  $R^3$ is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each $R^3$ optionally substituted with 1 to 5 substituents, each Ar is attached via an unsaturated carbon atom, wherein the substitutents are independently selected at each occurrence from: $C_1$–$C_{10}$ alkyl, $C_2$–$C_{10}$ alkenyl, $C_2$–$C_{10}$ alkynyl, $C_3$–$C_6$cycloalkyl, $C_4$–$C_{12}$ cycloalkylalkyl, $NO_2$, halo, CN, $C_1$–$C_4$ haloalkyl, $NR^6R^7$, $NR^8COR^7$, $NR^8CO_2R^7$, $COR^7$, $OR^7$, $CONR^6R^7$, $CO(NOR^9)R^7$, $CO_2R^7$, or $S(O)_nR^7$, where each such $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NO_2$, halo, CN, $NR^6R^7$, $NR^6COR^7$, $NR^7CO_2R^7$, $COR^7$ $OR^7$, $CONR^6R^7$, $CO_2R^7$, $CO(NOR^9)R^7$, or $S(O)_nR^7$;
  $R^5$ is selected from H, $C_1$–$C_4$ alkyl, $C_2$–$C_4$ alkenyl, $C_2$–$C_4$ alkynyl, $C_3$–$C_6$ cycloalkyl, $C_4$–$C_{10}$ cycloalkylalkyl, each optionally substituted with 1 to 3 substituents independently selected at each occurrence from $C_1$–$C_6$ alkyl, $C_3$–$C_6$ cycloalkyl; halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl; or halo, CN, —$NR^6R^7$, $NR^9COR^{10}$, —$NR^6S(O)_nR^7$, $S(O)_nNR^6R^7$, $C_1$–$C_4$ haloalkyl, —$OR^7$, SH or —$S(O)_nR^{12}$;

$R^6$, $R^{6a}$ and $R^7$ are independently selected at each occurrence from:

—H,

—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_{5-10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, -aryl, aryl($C_1$–$C_4$ alkyl), heteroaryl, heteroaryl($C_1$–$C_4$ alkyl), heterocyclyl or heterocyclyl ($C_1$–$C_4$ alkyl);

alternatively, $NR^6R^7$ and $NR^{6a}R^{7a}$ are independently piperidine, pyrrolidine, piperazine, N-methlpiperazine, morpholine or thiomorpholine, each optionally substituted with 1–3 $C_1$–$C_4$ alkyl groups;

$R^8$ is independently selected at each occurrence from H or $C_1$–$C_4$ alkyl;

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heterocyclyl is saturated or partially saturated heteroaryl, optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$;

n is independently at each occurrence 0, 1 or 2.

[10] The present invention also relates to a compound according to groups [1'] and [1]–[9] wherein $R^3$ is substituted with 2–4 substituents.

[11] The present invention also relates to a compound according to groups [1'] and [1]–[10] wherein $R^2$ is substituted with 1–4 substituents.

[12] The present invention also relates to a compound according to groups [1'] and [1]–[9] wherein $R^2$ is selected from 3-pentyl, $NEt_2$, butyl, $NHCH(CH_2OMe)_2$, $NHCH(CH_2OEt)_2$, $NHCH(Et)CH_2OMe$, NH-3-heptyl, NH-3-pentyl, NH-2-butyl, NH-3-hexyl, $NHCH(CH_2Ph)CH_2OMe$, $NHCH(Et)CH_2CH_2OMe$, NH-cyclobutyl, NH-cyclopentyl, NEtPr, NEtBu, NMePr, NMePh, $Npr_2$, $NPr(CH_2$-c-$C_3H_5)$, $N(CH_2CH_2OMe)_2$, morpholino, $N(CH_2Ph)CH_2CH_2OMe$, $N(Me)CH_2CH_2OMe$, $N(Et)CH_2CH_2OMe$, $N(CH_2$-c-$C_3H_5)CH_2CH_2OMe$, $N(CH_2$-c-$C_3H_5)Pr$, $N(CH_2$-c-$C_3H_5)Et$, OEt, $OCH(Et)CH_2OMe$, $OCH(Et)CH_2CH_2OMe$, OCH(Me)$CH_2CH_2OMe$, O-3-pentyl, O-2-pentyl, S-3-pentyl, S-2-pentyl, SEt, S(O)Et, $SO_2Et$, S-3-pentyl, S(O)-3-pentyl, $SO_{2-3}$-pentyl, S-2-pentyl, S(O)-2-pentyl, $SO_2$-2-pentyl, $CH(CO_2Et)_2$, $C(Et)(CO_2Et)_2$, $CH(Et)CH_2OH$, CH(Et)$CH_2OMe$, $CH(Et)CH_2CH_2OMe$, $CONMe_2$, $COCH_3$, COEt, COPr, CO-2-pentyl, CO-3-pentyl, $CH(OH)CH_3$, $C(OH)Me_2$, C(OH)Ph-3-pyridyl, $CH(OMe)CH_3$, CH(OMe)Et, CH(OMe)Pr, $CH(OEt)CH_3$, $CH(OPr)CH_3$, 2-pentyl, 2-butyl, cyclobutyl, cyclopentyl, CH(Me)cyclobutyl, CH(OMe)cyclobutyl, CH(OH)cyclobutyl, CH(Me)cyclopropyl, CH(OMe)cyclopropyl, CH(OH)cyclopropyl, CH(Et)cyclobutyl, CH(Et)cyclopropyl, CH(OMe)cyclobutyl, CH(OMe)cyclopropyl, CH(OEt)cyclobutyl, CH(OEt)cyclopropyl, $CH(Me)CH_2$-cyclobutyl, CH(OMe)$CH_2$-cyclobutyl, CH(OH)$CH_2$-cyclobutyl, $CH(Me)CH_2$-cyclopropyl, $CH(OMe)CH_2$-cyclopropyl, $CH(OH)CH_2$-cyclopropyl, $CH(Et)CH_2$-cyclobutyl, $CH(Et)CH_2$-cyclopropyl, $CH(OMe)CH_2$-cyclobutyl, $CH(OMe)CH_2$-cyclopropyl, $CH(OEt)CH_2$-cyclobutyl, $CH(OEt)CH_2$-cyclopropyl, $CH(CH_2OMe)$cyclobutyl, $CH(CH_2OMe)$cyclopropyl, $CH(CH_2OEt)$cyclobutyl, $CH(CH_2OEt)$cyclopropyl, $CH(cyclobutyl)_2$, $CH(cyclopropyl)_2$, CH(Et)$CH_2CONMe_2$, $CH(Et)CH_2CH_2Me_2$, $CH(CH_2OMe)Me$, $CH(CH_2OMe)Et$, $CH(CH_2OMe)Pr$, $CH(CH_2OEt)Me$, $CH(CH_2OEt)Et$, $CH(CH_2OEt)Pr$, $CH(CH_2C\equiv CMe)Et$, $CH(CH_2C\equiv CMe)Et$.

[13] The present invention further relates to a compound of formula I or Ia according to groups [1'] and [1]–[12] above wherein $R^3$ is selected from 2,4-$Cl_2$-Ph, 2,4,6-$Me_3$-Ph, 2,4-$Me_2$-Ph, 2-Me-4-MeO-Ph, 2-Cl-4-MeO-Ph, 2-Cl-4,5-(MeO)$_2$-Ph, 2-Cl-4-MeO-5-F-Ph, 2-Me-4-MeO-5-F-Ph, 2,5-(Me)$_2$-4-MeO-Ph, 2-Me-4-$NMe_2$-Ph, 2-$CF_3$-4-MeO-Ph, 2-Me-4-(COMe)-Ph, 2-Me-6-$Me_2$N-pyrid-3-yl, 4-Me-2-$Me_2$N-pyrid-5-yl, 2-Me-6-MeO-pyrid-3-yl, 4-Me-2-MeO-pyrid-5-yl.

[14] The present invention also relates to a compound of formula Ib

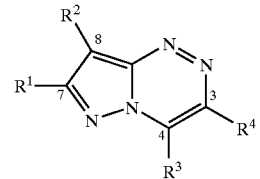

having $R^1$–$R^4$ as defined in groups [1]–[13] above.

[15] In a preferred embodiment, the present invention relates to a compound according to group [14] wherein $R^1$ is selected from H, $CH_3$, $C_2H_5$, $OCH_3$; $R_4$ is selected from H, $OCH_3$, $CH_3$ and $C_2H_5$; $R^2$ is selected from $CH(C_2H_5)_2$, $CH(c$-$C_3H_5)_2$, $CHC_2H_5(c$-$C_3H_5)$, $CH(C_2H_5)_2$, $CH(c$-$C_3H_5)_2$; and $R^3$ is selected from 2,4-$Cl_2$—Ph, 2-Cl-4-$CH_3O$—Ph, 2,4,6-$(CH_3)_3$—Ph, 2-Cl-4-$CF_3$—Ph and 2-$(CH_3)_2$N-4-$CH_3$-pyridin-5-yl.

[16] The present invention also relates to compounds of formula Ic, Id, Ie and If

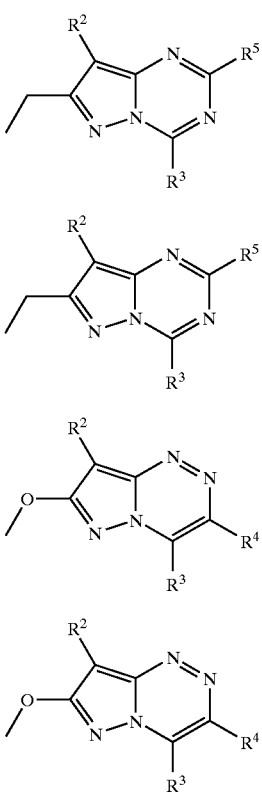

and the pharmaceutically acceptable salts thereof wherein $R^2$, $R^3$, $R^4$ and $R^5$ are as defined in groups [1]–[15] above.

[17] The present invention also relates to a method of antagonizing a CRF-1 receptor in mammals including humans wherein binding to the receptor causes and ultimately results in the treatment of affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of Formula I, Ia, Ib, Ic, Id, Ie or If according to groups [1]–[16] and [1'] above with the proviso that, in the case of compounds of group [1], provisos (a) and (b) are not present.

[18] The present invention also relates to use of a compound according to groups [1]–[16] and [1'] in therapy.

[19] The present invention also provides pharmaceutical compositions comprising compounds of Formula I, Ia, Ib, Ic, Id, Ie, or If with the variables as recited above in groups [1]–[16] and [1'] and a pharmaceutically acceptable carrier.

[20] The present invention also relates to compounds according to group [9] wherein $R^2$ is $NR^6R^7$, $OR^7$ or —$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$.

[21] The present invention also relates to a compound of formula II

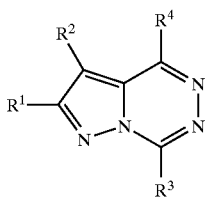

or a pharmaceutically acceptable salt or isomer thereof wherein $R^1$–$R^4$ and the other variables are as defined in groups [1'] and [1]–[20].

[22] The invention further relates to pharmaceutical compositions comprising the compound of group [21] and a pharmaceutically acceptable carrier.

[23] The invention also comprises use of a compound according to group [21] in therapy and to a method of treating a patient in need of treatment thereof comprising administering to said patient a pharmaceutically effective amount of a compound or composition according to group [21] or [22].

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. "Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl", is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., ═O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "pharmaceutically acceptable salts" includes acid or base salts of the compounds of formulas (I). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and the like.

The term "therapeutically effective amount" of a compound of this invention means an amount effective to antagonize abnormal level of CRF or treat the symptoms of affective disorder, anxiety, depression, immunological, cardiovascular or heart-related diseases and colonic hypersensitivity associated with psychopathological disturbance and stress in a host.

Syntheses

The variables as described in group [9] above are also shown in Schemes 1–4 which describe the synthesis of compounds of the invention.

Scheme 1

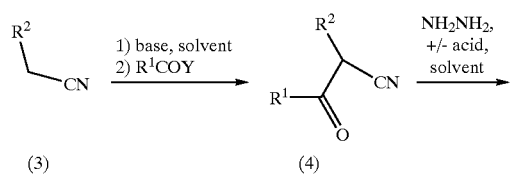

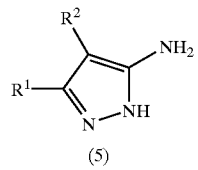

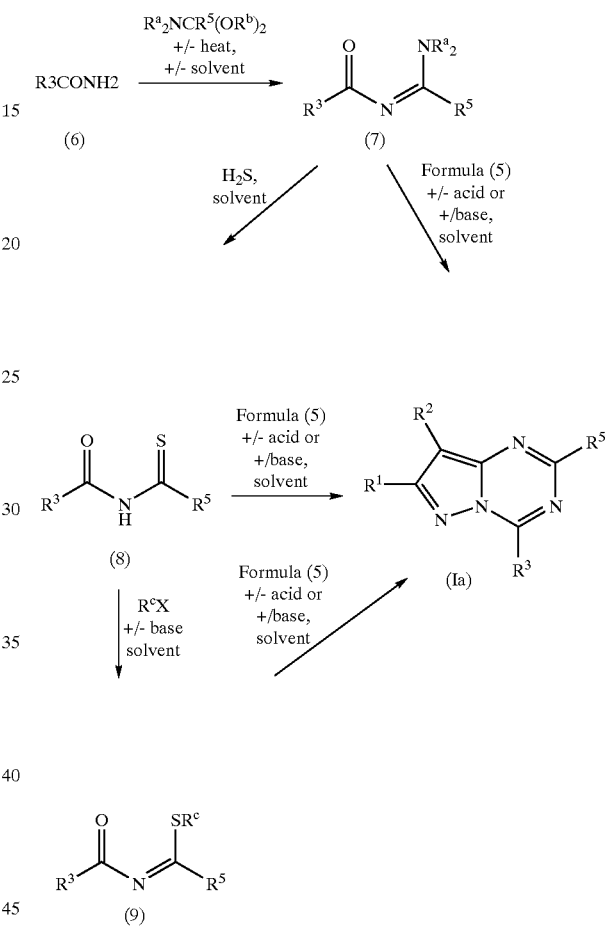

Some compounds of Formula (Ia), may be prepared from intermediate compounds of Formula (3) using the procedures outlined in Scheme 1 with the variables defined as above. Compounds of Formula (3) may be treated with a base in an inert solvent, followed by reaction with compounds of the Formula $R^1COY$, where $R^1$ is defined above and Y is a halogen, alkoxy, dialkylamino, alkylthio, alkanoyloxy, alkanesulfonyloxy or cyano group. Bases may include, but are not limited to, alkyl lithiums, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-diisopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 100° C. The resulting intermediates (4) are then reacted with hydrazine or its hydrate in an inert solvent in the presence or absence of an acid to provide pyrazoles (5). Inert solvents may include, but are not limited to, water, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Preferred temperatures range from ambient temperature to 150° C.

Compounds of Formula (Ia) may be prepared by reaction of pyrazoles (5) with intermediates (7), or (8) or (9) in the presence or absence of an acid or base in an inert solvent. Inert solvents may include, but are not limited to, water, alkyl alcohols (1 to 8 carbons, preferably methanol or-ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Bases may include, but are not limited to, alkali metal carbonates, alkali metal bicarbonates, trialkyl amines (preferably N,N-di-isopropyl-N-ethyl amine) or aromatic amines (preferably pyridine). Preferred temperatures range from ambient temperature to 150° C. Intermediates (7), (8) and (9) are derived from amides (6). Amides (6) may be reacted in an inert solvent in the presence or absence of an acid with compounds of the Formula $R^a{}_2NCR^5(OR^b)_2$, where $R^a$ and $R^b$ independently are lower alkyl, to generate compounds of Formula (7). Inert solvents may include, but are not limited to, water, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Preferred temperatures range from ambient temperature to 150° C. Intermediates of Formula (7) may be converted to compounds of Formula (8) by reaction with $H_2S$ in an inert solvent. Inert solvents may include, but are not limited to, water, alkyl alcohols (1 to 8 carbons, preferably methanol or ethanol), alkanoic acids of 2 to 10 carbons (preferably acetic acid), haloalkanoic acids (2–10 carbons, 1–10 halogens, such as trifluoroacetic acid), alkanesulfonic acids of 1 to 10 carbons (preferably methanesulfonic acid), hydrochloric acid, sulfuric acid, phosphoric acid or cyclic ethers (preferably tetrahydrofuran or 1,4-dioxane). Compounds of Formula (8) may be converted to compounds of Formula (9) by treatment with a base and an alkylating agent in an inert solvent at reaction temperatures ranging from −80° C. to 250° C. Bases may include, but are not limited to, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal carbonates, alkali metal hydroxides, alkali metal bis(trialkylsilyl)amides (preferably sodium bis(trimethylsilyl)amide), trialkyl amines (prefereably N,N-di-isopropyl-N-ethyl amine or triethyl amine) or aromatic amines (preferably pyridine). Alkylating agents may include, but are not limited to, $C_1$–$C_{10}$ alkyl-halides, -tosylates, -mesylates or -triflates or $C_1$–$C_{10}$ haloalkyl(1–10 halogens)-halides, -tosylates, -mesylates or -triflates. Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 100° C.

Compounds of Formula (Ia) may also be prepared by the methods shown in Scheme 2.

Scheme 2

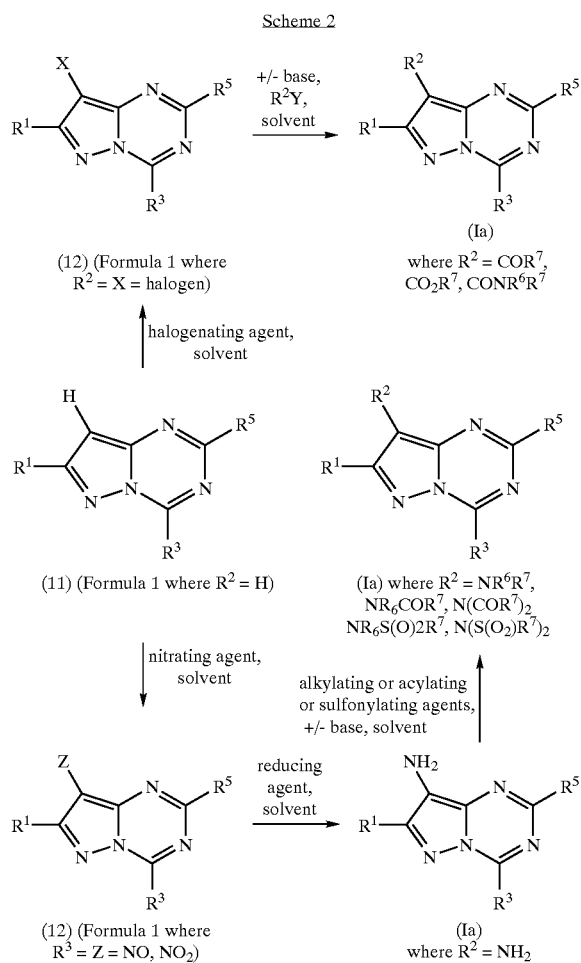

Compounds of Formula (11) may be treated with a halogenating agent in the presence or absence of a base in the presence or absence of an inert solvent at reaction temperatures ranging from −80° C. to 250° C. to give products of Formula (12) (where X is halogen). Halogenating agents include, but are not limited to, $Br_2$, $Cl_2$, $I_2$, N-bromosuccinimide, N-iodosuccinimide or N-chlorosuccinimide. Bases may include, but are not limited to, alkali metal carbonates, alkali metal bicarbonates, trialkyl amines (preferably N,N-di-isopropyl-N-ethyl amine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20° C. to 150° C. Compounds of Formula (12) may then be reacted with a base or a metal in the presence or absence of a metal salt in an inert solvent and then treated with a compound of the Formula $R^2Y$ where Y is halogen, alkoxy, dialkylamino, alkylthio, alkanoyloxy, alkanesulfonyloxy or cyano groups. Examples of bases include, but are not limited to, alkyl or aryl lithiums (e.g. n-butyl lithium or t-butyl lithium) or alkyl alkaline earth metal halides (e.g. MeMgBr). Examples of metals, include but are not limited to, alkali metals (e.g. Li) or alkali earth metals (e.g. Mg). Examples of metal salts include, but are not limited to, alkali metal halides, alkaline earth halides or transition metal halides such as $ZnCl_2$, $CeCl_3$ or CuI. Inert solvents may include, but are not limited to dialkyl ethers (preferably diethyl ether), cyclic ethers (preferably tetrahydrofuran or 1,4-dioxane), alkanes or aromatic hydrocarbons (preferably benzene or toluene. Preferred reaction temperatures range from −100° C. to 100° C.

Some compounds of Formula (Ia), where $R^2=NR^8COR^7$, $N(COR^7)_2$, $NR^8CONR^6R^7$, $NR^8CO_2R^{13}$ or $NR^6R^7$, may be prepared from intermediate compounds of Formula (11) (Formula (Ia) where $R^2=H$), using the procedures also outlined in Scheme 2. Compounds of Formula (11) may be treated with a nitrating or nitrosating agent in the presence or absence of an acid in an inert solvent at reaction temperatures ranging from −80° C. to 250° C. to give products of Formula (12) (where Z=NO or $NO_2$). Examples of nitrating agents include, but are not limited to, nitric acid, nitrous acid, alkali metal nitrates or nitrites (e.g. $KNO_3$ or $KNO_2$) or alkyl nitrites (e.g. isoamyl nitrite). Acids include, but are not limited to, alkanoic acids of 2 to 10 carbons (preferably acetic acid), haloacetic acids (e.g. trifluoroacetic acid), alkyl-, haloalkyl- or aryl-sulfonic acids (e.g. trifluoromethanesulfonic acid, p-toluenesulfonic acid or benzenesulfonic acid), alkanesulfonic acids of 1 to 10 carbons (preferably methanesulfonic acid), hydrochloric acid, sulfuric acid or phosphoric acid. Inert solvents may include, but are not limited to, water, alkyl alcohols (1 to 8 carbons, preferably methanol or ethanol), alkanes, dialkyl ethers (preferably glyme or diglyme), cyclic ethers (preferably tetrahydrofuran or 1,4-dioxane), aromatic hydrocarbons (preferably benzene or toluene). Compounds of Formula (12) may then be treated with a reducing agent in an inert solvent to provide compounds of Formula (1), where $R^2=NH_2$. Reducing agents include, but are not limited to, (a) hydrogen gas in combination with noble metal catalysts such as Pd-on-carbon, $PtO_2$, Pt-on-carbon, Rh-on-alumina or Raney nickel or (b) alkali metal or alkaline earth metal borohydrides (preferably lithium or sodium borohydride), borane, dialkylboranes (such as di-isoamylborane), alkali metal aluminum hydrides (preferably lithium aluminum hydride), alkali metal (trialkoxy)aluminum hydrides, or dialkyl aluminum hydrides (such as di-isobutylaluminum hydride). Inert solvents may include, but are not limited to, alkyl alcohols (1 to 6 carbons), dialkyl ethers (preferably diethyl ether), cyclic ethers (preferably tetrahydrofuran or 1,4-dioxane), aromatic hydrocarbons (preferably benzene or toluene). Preferred reaction temperatures range from −80° C. to 100° C. Compounds of Formula (Ia), where $R^2=NH_2$, may be converted by treatment with alkylating agents or acylating agents in the presence or absence of a base in an inert solvent to compounds of Formula (Ia), where $R^2=NR^6COR^7$, $N(COR^7)_2$, $NR^8CONR^6R^7$, $NR^6CO_2R^7$, $N(S(O)_2R^7)_2$, $NR^6S(O)_2R^7$ or $NR^6R^7$. Alkylating agents may include, but are not limited to, alkyl-halides, -tosylates, -mesylates or -triflates; $C_3$–$C_{10}$ alkenyl-halides, -tosylates, -mesylates or -triflates; $C_3$–$C_{10}$ alkynyl-halides, -tosylates, -mesylates or -triflates; $C_3$–$C_6$ cycloalkyl-halides, -tosylates, -mesylates or -triflates; $C_4$–$C_{12}$ cycloalkylalkyl-halides, -tosylates, -mesylates or -triflates; $C_5$–$C_{10}$ cycloalkenyl-halides, -tosylates, -mesylates or -triflates; or $C_6$–$C_{14}$ cycloalkenyl-halides, -tosylates, -mesylates or -triflates. Each of the above alkylating agents may be optionally substituted in a way consistent with the definition of $R^2$. Acylating agents may include, but are not limited to, acyl halides or anhydrides. Sulfonylating agents include, but are not limited to, sulfonyl halides or anhydrides. Each of the above acylating or sulfonylating agents may be optionally substituted in a way consistent with the definition of $R^2$. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis(trimethylsilyl)amide), trialkyl amines (prefereably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide) N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from –70° C. to 100° C.

Compounds of Formula (Ia), where $R^2=CR^6(OR^7)R^{6a}$, may be prepared by the procedures shown in Scheme 3.

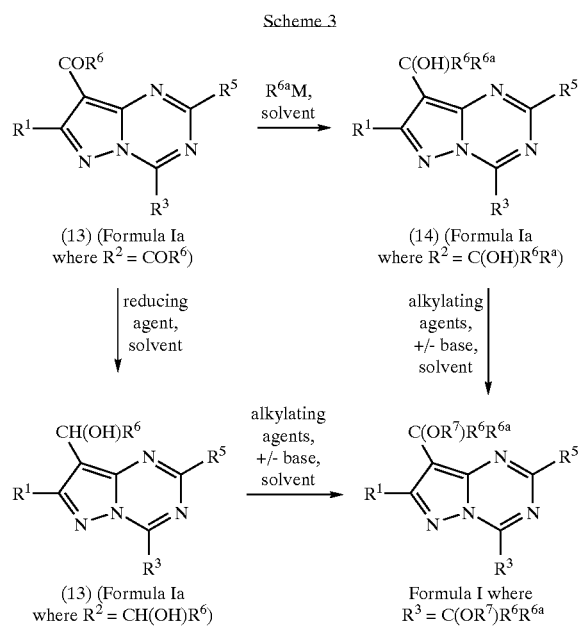

Scheme 3

(13) (Formula Ia where $R^2$ = $COR^6$)

(14) (Formula Ia where $R^2$ = $C(OH)R^6R^a$)

(13) (Formula Ia where $R^2$ = $CH(OH)R^6$)

Formula I where $R^3$ = $C(OR^7)R^6R^{6a}$

Compounds of Formula (13) (Formula 1 where $R^3=COR^6$) may be reacted with reagents of the Formula $R^{6a}M$ in an inert solvent, where $R^{6a}$ is defined above and M is alkali metal, ZnCl, ZnBr, ZnI, MgBr, MgCl, MgI, $CeCl_2$, or $CeBr_2$. Inert solvents may include, but are not limited to, dialkyl ethers (preferably diethyl ether), cyclic ethers (preferably tetrahydrofuran or 1,4-dioxane), or aromatic hydrocarbons (preferably benzene or toluene). Preferred reaction temperatures range from –70° C. to 100° C. The resulting intermediates (15) (Formula (Ia) where $R^2=CR^6(OH)R^{6a}$) may then be reacted with an alkylating agent in the absence or presence of a base in an inert solvent. Alkylating agents may include, but are not limited to, alkyl-halides, -tosylates, -mesylates or -triflates; $C_3-C_{10}$ alkenyl-halides, -tosylates, -mesylates or -triflates; $C_3-C_{10}$ alkynyl-halides, -tosylates, -mesylates or -triflates; $C_3-C_6$ cycloalkyl-halides, -tosylates, -mesylates or -triflates; $C_4-C_{12}$ cycloalkylalkyl-halides, -tosylates, -mesylates or -triflates; $C_5-C_{10}$ cycloalkenyl-halides, -tosylates, -mesylates or -triflates; or $C_6-C_{14}$ cycloalkenyl-halides, -tosylates, -mesylates or -triflates. Each of the above alkylating agents may be optionally substituted in a way consistent with the definition of $R^2$. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis(trimethylsilyl)amide), trialkyl amines (prefereably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from –70° C. to 100° C.

Alternatively, compounds of Formula (Ia), where $R^2=CR^6(OR^7)R^{6a}$, may be prepared by other procedures shown in Scheme 3. Compounds of Formula (13) (Formula Ia where $R^2=COR^6$) may be treated with a reducing agent in an inert solvent to afford intermediates of Formula (15) (Formula (Ia) where $R^2=CHR^6OH$). Reducing agents include, but are not limited to, (a) hydrogen gas in combination with noble metal catalysts such as Pd-on-carbon, $PtO_2$, Pt-on-carbon, Rh-on-alumina or Raney nickel or (b) alkali metal or alkaline earth metal borohydrides (preferably lithium or sodium borohydride), borane, dialkylboranes (such as di-isoamylborane), alkali metal aluminum hydrides (preferably lithium aluminum hydride), alkali metal (trialkoxy)aluminum hydrides, or dialkyl aluminum hydrides (such as di-isobutylaluminum hydride). Inert solvents may include, but are not limited to, alkyl alcohols (1 to 6 carbons), dialkyl ethers (preferably diethyl ether), cyclic ethers (preferably tetrahydrofuran or 1,4-dioxane), aromatic hydrocarbons (preferably benzene or toluene). Preferred reaction temperatures range from –80° C. to 100° C. Intermediates of Formula Formula (15) (Formula (Ia) where $R^2=CHR^6OH$)) may then be reacted with an alkylating agent in the presence or absence of a base in an inert solvent. Alkylating agents may include, but are not limited to, alkyl-halides, -tosylates, -mesylates or -triflates; $C_3-C_{10}$ alkenyl-halides, -tosylates, -mesylates or -triflates; ; $C_3-C_{10}$ alkynyl-halides, -tosylates, -mesylates or -triflates; $C_3-C_6$ cycloalkyl-halides, -tosylates, -mesylates or -triflates; $C_4-C_{12}$ cycloalkylalkyl-halides, -tosylates, -mesylates or -triflates; $C_5-C_{10}$ cycloalkenyl-halides, -tosylates, -mesylates or -triflates; or $C_6-C_{14}$ cycloalkenyl-halides, -tosylates, -mesylates or -triflates. Each of the above alkylating agents may be optionally substituted in a way consistent with the definition of $R^2$. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis (trimethylsilyl)amide), trialkyl amines (prefereably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from −70° C. to 100° C.

In addition to the specific and generic groups on compounds Ia as shown above in Schemes 1–3, the additional compounds within the generic scope having a compound of formula Ia with $R^1$–$R^5$ as described or recited in group [1] may be made according to the general procedures described in these schemes using the appropriate starting materials and as described in the specific examples as well.

The embodiment of this invention concerning compounds of Formula (Ib) with the structure

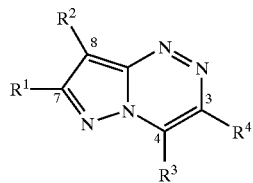

may be prepared according to the following method:

The method of Ege and Gilbert, *J. Het. Chem.* 1981, 18, 675–677, is used to prepare the desired ring system (Scheme 4). Thus, aminopyrazole 4-A is converted to diazonium salt 4-B, using sodium nitrite/acid or such reagents as isoamylnitrite. The diazonium salt is condensed with a phosphorus ylide compound 4-C to give the pyrazolo[5,1-c] [1,2,4] triazine product.

Scheme 4

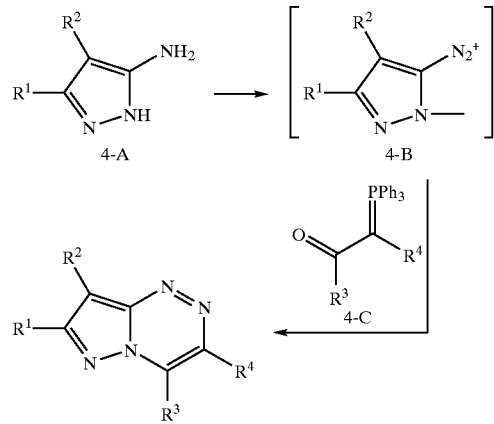

Some compounds of Formula (Ia), may be prepared from intermediate compounds of Formula (3) using the procedures outlined in Scheme 5 with the variables defined as above. Compounds of Formula (5) may be treated with compounds of the Formula $R^5(N=H)(OR')$, where R' is lower alkyl or their acid-addition salts, in the presence or absence of a base in an inert solvent. Bases may include, but are not limited to, alkyl lithiums, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis (trialkylsilyl)amides (preferably sodium bis(trimethylsilyl) amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 100° C. The resulting intermediates are then treated with compounds of the Formula R3COY, where Y is halogen or lower alkoxy, in the presence or absence of a base in an inert solvent to provide compounds of the Formula (Ia). Bases may include, but are not limited to, alkyl lithiums, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 100° C.

SCHEME 5

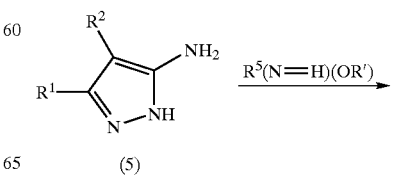

(5)

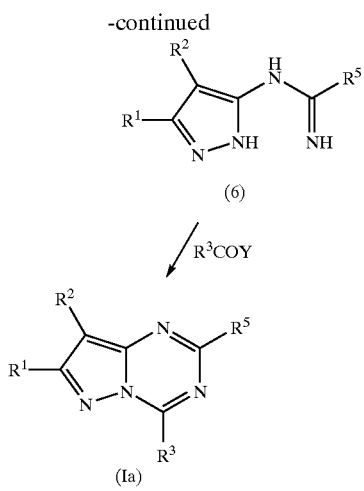

Compounds of formula II as described above are also readily prepared according to the general procedure described in Scheme 6. This procedure is described generally in *J. Het. Chem* 1981, 1319.

SCHEME 6

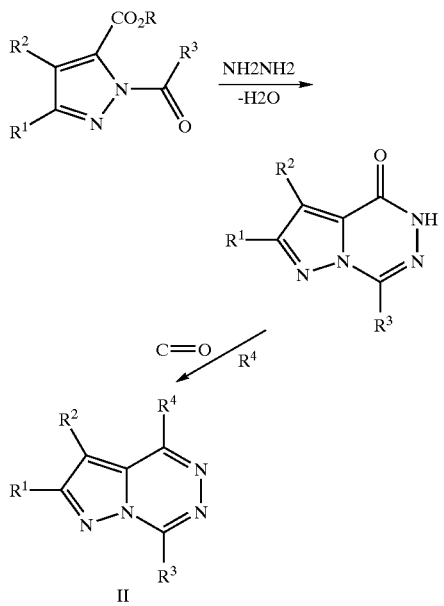

The following specific synthetic examples describe the procedures described generically above which, when applied to appropriately substituted substrates, were and may be employed in the synthesis of the compounds in Table 1.

EXAMPLES

Analytical data were recorded for the compounds described below using the following general procedures. Proton NMR spectra were recorded on an Varian FT-NMR (300 MHz); chemical shifts were recorded in ppm (δ) from an internal tetramethysilane standard in deuterochloroform or deuterodimethylsulfoxide as specified below. Mass spectra (MS) or high resolution mass spectra (HRMS) were recorded on a Finnegan MAT 8230 spectrometer (using chemi-ionization (CI) with $NH_3$ as the carrier gas or gas chromatography (GC) as specified below) or a Hewlett Packard 5988A model spectrometer. Melting points were recorded on a Buchi Model 510 melting point apparatus and are uncorrected. Boiling points are uncorrected. All pH determinations during workup were made with indicator paper.

Reagents were purchased from commercial sources and, where necessary, purified prior to use according to the general procedures outlined by D. Perrin and W. L. F. Armarego, *Purification of Laboratory Chemicals*, 3rd ed., (New York: Pergamon Press, 1988). Chromatography (thin layer (TLC) or preparative) was performed on silica gel using the solvent systems indicated below. For mixed solvent systems, the volume ratios are given. Otherwise, parts and percentages are by weight.

Example 1

4-(2,4-dichlorophenyl)-8-(3-pentyl)-7-ethyl-2-methyl-pyrazolo[1,5-a]-1,3,5-triazine (Formula Ia, $R^1$ is ethyl, $R^5$ is methyl, $R^2$ is 3-pentyl, $R^3$ is 2,4-dichlorophenyl).

A. N-(1-(Dimethylamino)ethylidene)-2,4-dichlorobenzamide

A mixture of 2,4-dichlorobenzamide (1.9 g, 10 mmol) and N,N-dimethylformamide dimethyl acetal (3.5 g, 3.8 mL, 26 mmol) was heated at 120° C. and stirred under a nitrogen atmosphere for 2 h. After being cooled to room temperature, the reaction mixture was concentrated in vacuo to afford an oil. Medium pressure chromatography on silica gel (EtOAc:hexanes: 1:3 to 1:1) and removal of solvent in vacuo afforded a solid (2.03 g, 78% yield): NMR ($CDCl_3$, 300 MHz): δ 7.73 (d, 1H, J=8), 7.39 (d, 1H, J=2), 7.24 (dd, 1H, J=8,2), 3.16 (s, 3H), 3.13 (s, 3H), 2.39 (s, 3H).

B. N-(Thioacetyl)-2,4-dichlorobenzamide

Hydrogen sulfide was bubbled through glacial acetic acid (20 mL) for approximately 5 min. The above intermediate was added portionwise over 5 min. Additional hydrogen sulfide was bubbled through the reaction mixture for approximately 10 min. Nitrogen was then bubbled through the reaction mixture. Dilution with water (25 mL) caused a precipitate to form. The solid was collected by filtration, washed with copious amounts of water and dried in vacuo. The resulting solid (1.75 g, 90% yield) was used without further purification: NMR ($CDCl_3$, 300 MHz): δ 9.9 (br s, 1H), 7.68 (d, 1H, J=8), 7.51 (d, 1H, J=2), 7.40 (dd, 1H, J=9,2), 3.10 (s, 3H).

C. 3-Amino-5-ethyl-4-(3-pentyl)pyrazole

A mixture of NaCN (4.1 g, 82.7 mmol) and KI (154 mg, 0.9 mmol) in anhydrous dimethylsulfoxide (40 mL) was heated to 40° C. with stirring. 3-Ethyl-1-bromobutane (12.4 g, 75.2 mmol) was added dropwise over 10 min. The reaction mix was first heated to 80° C. and stirring was continued for 1 h, then to 120° C. and stirred for 5 h. The reaction mix was cooled to ambient temperature and a precipitate formed. Dilution with water (150 mL), extraction with ether (3×100 mL), washing the combined organic layers with a saturated NaCl solution, drying over MgSO4 and filtration afforded a solution. Removal of solvent in vacuo provided 3-ethylpentanenitrile (7.4 g, 89% yield): NMR ($CDCl_3$, 300 MHz): δ 2.33 (d, 2H, J=6), 1.45–1.40 (m, 5H), 0.92 (t, 6H, J=7).

A solution of di-isopropylamine (14.8 g, 20.5 mL, 147 mmol) in anhydrous THF (40 mL) was cooled to −78° C. with stirring under a nitrogen atmosphere. A solution of n-butyl lithium in hexanes (1.6M, 87.5 mL, 140 mmol) was added dropwise over 15 min. The resulting solution was stirred for an additional 30 min. A solution of 3-ethylpentanenitrile (7.4 g, 67 mmol) in THF (30 mL) was added dropwise over 15 min and then the reaction mixture was stirred for 30 min. A solution of ethyl propionate (6.8 g, 7.6 mL, 67 mmol) in THF (20 mL) was added dropwise; then the reaction mixture was warmed with stirring to ambient temperature over 3 h. The mix was poured onto water (200 mL) and the pH was adjusted to ~4 by the slow addition of a concentrated Hcl solution. Three extractions with ether (100 mL), drying the combined organic layers over MgSO4, filtration and removal of solvent in vacuo provided an oil (9.53 g): NMR (CDCl$_3$,300 MHz): δ 3.50 (d, 1H, J=4), 2.74 (q, 2H, J=7), 1.85–1.75 (m, 1H), 1.45–1.35 (m, 4H), 1.12 (t, 3H, J=7), 1.0–0.8 (m, 6H).

A mixture of the above intermediate (7.0 g), hydrazine hydrate (2.30 g, 2.23 mL, 46 mmol) and glacial acetic acid (1 mL) in toluene was heated to reflux temperature in a Dean-Stark apparatus and stirred for 16 h. The reaction mixture was cooled to ambient temperature and solvent was removed in vacuo. EtOAc (100 mL) was added to the residue and the resulting solution was washed three times with a saturated NaHCO3 solution (25 mL). The organic solution was dried over MgSo4, filtered and concentrated in vacuo to provide an oil (6.7 g, 88% overall yield): NMR (CDCl$_3$,300 MHz): δ 2.53 (q, 2H, J=7), 1.70–1.50 (m, 5H), 1.20 (t, 3H, J=7), 0.83 (t, 6H, J=7).

D. A mixture of N-(thioacetyl)-2,4-dichlorobenzamide (200 mg, 0.81 mmol) and 3-amino-5-ethyl-4-(3-pentyl)pyrazole (146 mg, 0.81 mmol) in dioxan (1 mL) was stirred at reflux temperature for 16 h. After being cooled to room temperature, the reaction mixture was concentrated in vacuo. Preparative TLC using EtOAc:hexanes::1:1 generated the title product (77.3 mg, 24% yield): mp=91–93° C.; NMR (CDCl$_3$,300 MHz): δ 7.64 (d, 1H, J=8), 7.57 (d, 1H, J=2), 7.44 (dd, 1H, J=8,2), 2.77 (q, 2H, J=8), 2.69 (s, 3H), 2.80–2.60 (m, 1H), 2.00–1.80 (m, 4H), 1.25 (t, 3H, J=8), 0.82 (t, 6H, J=7); CI-HRMS m/z Calcd: 377.1294, Found: 377.1303.

Example 1a 4-(2.4-dichlorophenyl)-8-(3-pentyl)-7-ethyl-2-methyl-pyrazolo[1,5-a]-1,3,5-triazine Alternate Preparation of (Formula Ia, R$^1$ is ethyl, R$^5$ is methyl, R$^2$ is 3-pentyl, R$^3$ is 2,4-dichlorophenyl)

A. N-(1-(Methylthio)ethylidene)-2,4-dichlorobenzamide

A mixture of N-(thioacetyl)-2,4-dichlorobenzamide (400 mg, 1.6 mmol) and K2CO3 (445 mg, 3.22 mmol) in anhydrous acetonitrile (20 mL) was stirred at ambient temperature. Iodomethane (458 mg, 0.2 mL, 3.22 mmol) was added and the reaction mixture was then stirred for 2.5 h. Solvent was removed in vacuo and the residue was partitioned between ether and water. The combined organic layers were dried over MgSO4, filtered and concentrated in vacuo to give an oil (406 mg): NMR (CDCl$_3$,300 MHz): δ 7.86 (d, 1H, J=8), 7.47 (d, 1H, J=2), 7.32 (dd, 1H, J=8, 2), 2.40 (s, 3H), 2.29 (s, 3H).

B. A mixture of N-(1-(methylthio)ethylidene)-2,4-dichlorobenzamide (100 mg, 0.38 mmol) and 3-amino-5-ethyl-4-(3-pentyl)pyrazole (69 mg, 0.38 mmol) in dioxan (1 mL) was stirred at reflux temperature for 2 h. After being cooled to room temperature, the reaction mixture was concentrated in vacuo. Preparative TLC using EtOAc:hexanes::1:1 generated the title product (68 mg, 47% yield), which was identical to the product obtained by the method described in Example 1.

Example 2

4-(2,4-dichlorophenyl)-8-diethylamino-7-ethyl-2-methyl-pyrazolo[5-a]-1,3,5-triazine (Formula 1, R$^1$ is ethyl, R$^5$ is methyl, R$^2$ is diethylamino, R$^3$ is 2,4-dichlorophenyl)

A. 4-(2,4-dichlorophenyl)-7-ethyl-2-methyl-pyrazolo[1,5-a]-1,3,5-triazine

A mixture of 3-amino-5-ethylpyrazole (10.3 g, 39.3 mmol) and N-(1-(methylthio)ethylidene)-2,4-dichlorobenzamide (4.0 g, 35.7 mmol) in anhydrous dioxan (20 mL) was stirred at reflux temperature under a nitrogen atmosphere for 16 h. After being cooled to ambient temperature, the reaction mix was concentrated in vacuo and the residue was treated with dichloromethane. The resulting supsension was filtered and the filtrate was concentrated in vacuo to afford an oil (1.5 g, 14% yield): NMR (CDCl$_3$,300 MHz): δ 7.62 (d, 1H, J=8), 7.59 (d, 1H, J=2), 7.45 (dd, 1H, J=8,2), 6.42 (s, 1H), 2.82 (q, 2H, J=8), 2.73 (s, 3H), 1.30 (t, 3H, J=8).

B. 4-(2,4-dichlorophenyl)-7-ethyl-2-methyl-8-nitro-pyrazolo[1,5-a]-1,3,5-triazine A solution of 4-(2,4-dichlorophenyl)-7-ethyl-2-methyl-pyrazolo[1,5-a]-1,3,5-triazine (653 mg, 2.2 mmol) in acetic anhydride (4 mL) was cooled with stirring to −5 to −10° C. A solution of fuming nitric acid (160 mg, 2.55 mmol) in acetic anhydride (2 mL) was added dropwise over 15 min. The reaction mixture was stirred at the same temperature for 3 h, then it was partitioned between water and ether three times. The combined organic layers were washed with a saturated NaHCO3 solution, dried over MgSO4 and filtered. Solvent was removed in vacuo to provide a solid. Column chromatography (EtOAc:hexanes::1:9 to 1:4) provided a solid (166 mg, 21% yield) after removal of solvent in vacuo: NMR (CDCl$_3$, 300 MHz): δ 7.64 (d, 1H, J=8), 7.63 (d, 1H, J=2), 7.50 (dd, 1H J=8, 2), 3.19 (q, 2H, J=7), 2.94 (s, 3H), 1.32 (t, 3H, J=7).

B. 4-(2,4-dichlorophenyl)-7-ethyl-2-methyl-8-amino-pyrazolo[1,5-a]-1,3,5-triazine A mixture of the above intermediate (160 mg, 0.45 mmol), Na2S2O4 (554 mg, 3.2 mmol), concentrated ammonium hydroxide (0.1 mL) in dioxan (8 mL) was stirred at ambient temperature for 30 min. The reaction mixture was concentrated in vacuo and the residue was partitioned between ether and water three times. The organic layers were combined, dried over MgSO4, filtered and concentrated in vacuo to give a solid (92.5 mg, 64% yield): NMR (CDCl$_3$, 300 MHz): δ 7.60 (d, 1H, J=8), 7.57 (d, 1H, J=2), 7.43 (dd, 1H, J=8,2), 2.79 (q, 2H, J=8), 2.63 (s, 3H), 1.30 (t, 3H, J=8)

C.

A mixture of the above intermediate (46 mg, 0.14 mmol), ethyl triflate (64 mg, 46 μL, 0.36 mmol) and i-Pr2NEt (46 mg, 62 μL, 0.36 mmol) in dichloromethane (1 mL) was stirred at room temperature for 2 h. Solvent was removed in vacuo. Column chromatography (EtOAc:hexanes::1:9) generated the title compound, a solid (30.1 mg, 57% yield): mp=98–99° C.: NMR (CDCl$_3$, 300 MHz): δ 7.63 (d, 1H, J=8), 7.57 (d, 1H, J=2), 7.44 (dd, 1H, J=8, 2), 3.22 (q, 4H, J=7), 2.77 (q, 2H, J=8), 2.69 (s, 3H), 1.25 (t, 3H, J=8), 1.00 (t, 6H, J=8); CI-HRMS m/z Calcd: 378.1252; Found: 378.1274.

Using the above procedures and modifications known to one skilled in the art of organic synthesis, the following examples of Table 1 were or may be prepared. The examples delineated in Table 1 may be prepared by the methods outlined in Examples 1, 2 or 3 or combinations thereof. Commonly used abbreviations are: Ph is phenyl, Pr is propyl, Me is methyl, Et is ethyl, Bu is butyl, Ex is Example, amorph. is amorphous. In Table 1, unless otherwise indicated, the examples with the physical data shown are based upon structure Ic. Example 10, described below, shows a detailed preparation of a 1,2,4 triazine. Table 1 also shows the preferred examples having structures Ie and If that can readily be made according to the procedure delinated below for Example 10.

Example 10

4-(2,4-dichlorophenyl)-7-ethyl-8-(3-pentyl)pyrazolo [5,1-c][1,2,4]triazine

Part A. A mixture of 2-ethyl-1-bromobutane (10.0 mL, 71.4 mmol), potassium cyanide (14.0 g, 215 mmol) and aliquat 336 (10 drops) in 50 mL water was heated to reflux overnight with vigorous stirring. The mixture was cooled, and extracted with dichloromethane (2×50 mL). The extracts were combined, dried over magnesium sulfate, filtered and evaporated. The residual liquid was distilled bulb-to-bulb to afford pure product, 3-ethylpentanenitrile (5.50 g, 49.5 mmol, 69%). b.p. 40–45 ° C. (5 mm Hg). Spectral: $^1$H NMR (300 MHz, CDCl$_3$): δ2.33 (2H, d, J=5.8 Hz), 1.62–1.36 (5H, m), 0.92 (6H, t, J=7.3 Hz). MS (H$_2$O-GC/MS): m/e 112 (100).

Part B. A solution of diisopropylamine (7.50 mL, 57.2 mmol) in THF (100 mL) was cooled to −78° C., and treated with n-butyllithium (34.0 mL of a 1.6 M solution in hexane). The solution was warmed briefly to 0° C., and then recooled to −78° C. The nitrile compound from Part A was then added by syringe, and the solution was allowed to stir for 1 hour. Then, ethyl propionate (6.50 mL, 56.7 mmol) was added by syringe, and the resulting mixture was allowed to stir and warm to ambient temperature for 12 hours. It was poured into 200 mL of satd. aq. NH$_4$Cl solution, and this was extracted with ethyl acetate (2×200 mL). The extracts were combined, dried over magnesium sulfate, filtered and evaporated. The residual oil was separated by column chromatography (silica gel, 10:90 ethyl acetate-hexane) to afford the product, 4-cyano-5-ethyl-3-heptanone, as an oil 4.06 g, 24.3 mmol, 49%). TLC R$_F$ 0.47 (20:80 ethyl acetate-hexane). Spectral data: $^1$H NMR (300 MHz, CDCl$_3$): δ 3.49 (1H, d, J=4.4 Hz), 2.74 (2H, q, J=7.3 Hz), 2.08–1.98 (1H, m), 1.70–1.58 (1H, m), 1.50–1.20 (3H, m), 1.12 (3H, t, J=7.3 Hz), 0.95 (3H, t, J=7.3 Hz), 0.91 (3H, t, J=7.3 Hz). MS (H$_2$O-GC/MS): m/e 167 (100).

Part C. A solution of the ketonitrile from Part B (4.06 g, 24.3 mmol), hydrazine hydrate (2.70 mL, 55.7 mmol) and acetic acid (5.00 mL, 83.7 mmol) in benzene (50 mL) was heated to reflux under a Dean-Stark trap with azeotropic distillation of water. After being heated for 12 hours, the mixture was cooled and poured into 100 mL 1 N aq. NaHCO$_3$ solution. This was extracted with ethyl acetate (2×100 mL), and the extracts were washed in sequence with brine, combined, dried over sodium sulfate, filtered and evaporated to afford sufficiently-pure product, 3-amino-5-ethyl-4-(3-pentyl) pyrazole, as a viscous oil (2.48 g, 13.7 mmol, 56%). Spectral data: $^1$H NMR (300 MHz, CDCl$_3$): δ 3.48 (2H, br), 2.54 (2H, q, J=7.3 Hz), 2.25–2.14 (1H, m), 1.71–1.49 (4H, m), 1.20 (3H, t, J=7.3 Hz), 0.83 (6H, t, J=7.3 Hz), 1H missing. MS (NH$_3$–CI): m/e 183 (12), 182 (100).

Part D. A solution of 3-amino-5-ethyl-4-(3-pentyl)pyrazole (0.750 g, 4.14 mmol) was suspended in 4 mL water and made acidic with conc. aq. HCl (2 mL). This was cooled in an ice bath, and a conc. aq. solution of sodium nitrite (0.286 g, 4.14 mmol) was added dropwise. After stirring for 30 min., the mixture was diluted with ice-cold dichloromethane (40 mL) and made alkaline with a saturated solution of sodium carbonate in water. The organic layer was separated, dried over sodium sulfate and filtered. The filtrate was then delivered dropwise to a stirring solution of 2,4-dichlorobenzoyl)methylenetriphenylphosphorane (Bauer, et al., J. Het. Chem. 1998, 35, 81–87) (1.86 g, 4.14 mmol) in dichloromethane at 10° C. After stirring for 10 hrs. with warming to ambient temperature, the reaction mixture was evaporated, and the residual material was separated by column chromatography (silica gel, 15:85 ethyl acetate-hexane) to afford the title product (0.124 g, 8.2%) as orange crystals (m.p. 116.7–117.8° C.). TLC R$_f$ 0.51 (20:80 ethyl acetate-hexane).

This procedure can be utilized to make compounds of formula Ib having the variables as defined in group [1] above by appropriately substituting or preparing any of the different variables for R$^1$, R$^2$, R$^3$, R$^4$ including substituted versions thereof as defined in group [1] or any of the more preferred groups.

Example 11

4-phenyl-8-(3-pentyl)-7-ethyl-2-methyl-pyrazolo[1, 5-a]-1,3,5-triazine (Formula Ia, R$^1$ is ethyl, R$^5$ is methyl, R$^2$ is 3-pentyl, R$^3$ is phenyl).

Ethyl acetimidate hydrochloride (656 mg, 5.31 mmol) was added to a solution of K$_2$CO$_3$ (734 mg, 5.31 mmol) in H$_2$O (2 mL) in a separatory funnel. The aqueous layer was extracted with CH$_2$Cl$_2$ (3×1 mL) to form the free base. The combined organic layers were dried with Na$_2$SO$_4$, and filtered through a plug of cotton. The CH$_2$Cl$_2$ extract was transferred directly into a 15 mL round bottom flask containing of 3-amino-5-ethyl-4-(3-pentyl)pyrazole (300 mg, 1.77 mmol). Acetonitrile (1.5 mL, anhydrous) was added followed by HOAc (0.112 mL, 1.95 mmol) and the mixture was stirred overnight at room temperature. The solid was collected by filtration to give 358 mg (96% yield) of 3-acetamidino-5-ethyl-4-(3-pentyl)pyrazole, hydrochloride salt as a white solid: mp=168.5–171.5° C., $^1$H NMR, 300 MHz (D$_2$O) δ 2.51 (q, J=7.7 Hz, 2H), 2.24 (s, 3H), 2.21–2.15 (m, 1H), 1.72 (s, 3H), 1.52–1.43 (m, 2H), 1.33–1.22 (m, 2H), 1.02 (t, J=7.7Hz, 3H), 0.56 (t, J=7.3 Hz, 6H), CI-MS (NH$_3$) m/e 223.2 [(M+H–HOAc)$^+$; calcd for C$_{12}$H$_{23}$N$_4$: 223.2].

To a solution of K$_2$CO$_3$ (48 mg, 0.35 mmol) in H$_2$O (3 mL) in a separatory funnel was added 3-acetamidino-5-ethyl-4-(3-pentyl)pyrazole, hydrochloride salt (60 mg, 0.212 mmol). The aqueous layer was extracted with CH$_2$Cl$_2$ (4×5 mL). The combined organic layers were washed with brine, dried over Na$_2$SO$_4$, filtered, and concentrated to give the free base of the pyrazole (39 mg, 0.175 mmol). This intermediate (39 mg, 0.175 mmol) was dissolved in dioxane (1 mL) and a solution of benzoyl chloride (30 mg, 0.210 mmol) in dioxane (1 mL) was added via cannula followed by the addition of a catalytic amount of 4-dimethylaminopyridine. The mixture was stirred at room temperature for 15 min (turned cloudy then clear) and was subsequently heated at reflux (112° C.) for 15 h. The mixture was cooled to room temperature and concentrated. The residue was purified via preparative thin layer chromatography (silica gel, 1 mm thickness) using 20% EtOAC in hexanes to give 29 mg (54% yield) of the title compound as a yellow oil: $R_f$=0.66, $^1$H NMR, 300 MHz (CDCl$_3$) δ 8.75–8.71 (m, 2H), 7.64–7.53 (m, 3H), 2.85 (q, J=7.7 Hz, 2H), 2.72–2.62 (m, 1H), 2.70 (s, 3 H), 1.97–1.76 (m, 4H), 1.37 (t, J=7.6 Hz, 3H), 0.82 (t, J=7.3 Hz, 6H), LRMS (CI, NH$_3$) m/e 309.2 [(M+H)$^+$; calcd for C$_{19}$H$_{25}$N$_4$: 309.2].

Example 12

4-phenyl-8-(3-pentyl)-7-ethyl-2-methyl-pyrazolo [1,5-a]-1,3,5-triazine (Formula Ia, R$^1$ is ethyl, R$^5$ is methyl, R$^2$ is 3-pentyl, R$^3$ is 2-methyl-4-chlorophenyl).

To a solution of K$_2$CO$_3$ (48 mg, 0.35 mmol) in H$_2$O (3 mL) in a separatory funnel was added 3-acetamidino-5-ethyl-4-(3-pentyl)pyrazole, hydrochloride salt (49 mg, 0.174 mmol). The aqueous layer was extracted with CH$_2$Cl$_2$ (4×5 mL). The combined organic layers were washed with brine, dried over Na$_2$SO$_4$, filtered, and concentrated to give the free base of 2 (31 mg, 0.139 mmol). This intermediate was dissolved in dioxane (1 mL) and a solution of 4-chloro-2-methylbenzoyl chloride (32 mg, 0.167 mmol) in dioxane (1 mL) was added via cannula followed by the addition of a catalytic amount of 4-dimethylaminopyridine. The mixture was stirred at room temperature for 15 min (turned cloudy then clear) and was subsequently heated at reflux (112° C.) for 15 h. The mixture was cooled to room temperature and concentrated. The residue was purified via preparative thin layer chromatography (silica gel, 1 mm thickness) using 10% EtOAC in hexanes to give 14 mg (28% yield) of the title compound as a yellow solid: $R_f$=0.40, mp =84.5–86.5° C., $^1$H NMR, 300 MHz (CDCl$_3$) δ 7.64 (d, J=8.1 Hz, 1H), 7.35 (s, 1H), 7.34 (d, J=7.7 Hz, 1H), 2.77 (q, J=7.7 Hz, 2H), 2.68 (s, 3H), 2.67–2.60 (m, 1H), 2.28 (s, 3H), 1.97 (m, 4H), 1.25 (t, J=7.7 Hz, 3H), 0.82 (t, J=7.3 Hz, 6H), CI-MS (NH$_3$) m/e 357.1 [(M +H)$^+$; calcd for C$_{20}$H$_{26}$N$_4$Cl: 357.2].

Example 13

4-(2-chloro-4-methylsulfonylphenyl)-8-(3-pentyl)-7-ethyl-2-methyl-pyrazolo[1,5-a]-1,3,5-triazine (Formula Ia, R$^1$ is ethyl, R$^5$ is methyl, R$^2$ is 3-pentyl, R$^3$ is 2-methyl-4-methylsulfonylphenyl).

To a solution of K$_2$CO$_3$ (280 mg, 2.03 mmol) in H$_2$O (15 mL) in a separatory funnel was added 3-acetamidino-5-ethyl-4-(3-pentyl)pyrazole, hydrochloride salt (250 mg, 1.12 mmol). The aqueous layer was extracted with CH$_2$Cl$_2$ (4×15 mL). The combined organic layers were washed with brine, dried over Na$_2$SO$_4$. filtered, and concentrated to give the free base of 3-acetamidino-5-ethyl-4-(3-pentyl)pyrazole, hydrochloride salt (225 mg, 1.01 mmol). This intermediate was dissolved in dioxane (2 mL) and a solution of 2-chloro-4-methanesulfonylbenzoyl chloride (307 mg, 1.21 mmol) in dioxane (2 mL) was added via cannula followed by the addition of DMAP (cat.). The mixture was stirred at room temperature for 15 min (turned cloudy then clear) and was subsequently heated at reflux (112° C.) for 15 h. The mixture was cooled to room temperature and concentrated. The residue was purified via prep plate using 50% EtOAc in hexanes to give 95 mg (22% yield) of the title compound as a yellow solid: $R_f$=0.61, mp=172.3–173.8° C., $^1$H NMR, 300 MHz (CDCl$_3$) d 8.14 (d, J=1.4 Hz, 1H), 8.03 (dd, J=6.6, 1.5 Hz, 1H), 7.91 (d, J=8.0 Hz, 1H), 3.13 (s, 3H), 2.78 (q, J=7.6 Hz, 2H), 2.70 (s, 3H), 2.71–2.59 (m, 1H), 2.00–1.77 (m, 4H), 1.25 (t, J=7.5 Hz, 3H), 0.83 (t, J=7.5 Hz, 6H), ESI-MS m/e 421.0 [(M+H)$^+$; calcd for C$_{20}$H$_{26}$N$_4$O$_2$SCl: 421.1.

TABLE 1

| Ex. | Formula | R$^5$ | R$^4$ | R$^2$ | R$^3$ | mp (° C.) |
|---|---|---|---|---|---|---|
| 1 | Ic | Me | — | 3-pentyl | 2,4-Cl$_2$—Ph | 91–93 |
| 3 | Ic | Me | — | NEt$_2$ | 2,4-Cl$_2$—Ph | 98–99 |
| 4 | Ic | Me | — | 3-pentyl | 2-Me-4-MeO—Ph | 65–67 |
| 5 | Ic | Me | — | 3-pentyl | 2-Cl-4,5-(MeO)$_2$—Ph | 104–105 |
| 6 | Ic | Me | — | 3-pentyl | 2-Cl-4-MeO-5-F—Ph | 94–97 |

TABLE 1-continued

| | | | | | | |
|---|---|---|---|---|---|---|
| 7 | Ic | Me | — | 3-pentyl | 2-Me-4-MeO-5-F—Ph | 105–107 |
| 8 | Ic | Me | — | 3-pentyl | 2,6-Me$_2$-pyrid-3-yl | oil |
| 9 | Ic | Me | — | butyl | 2,4-Cl$_2$—Ph | amorph. |
| 10 | Ie | — | H | 3-pentyl | 2,4-Cl$_2$—Ph | — |
| 11 | Ic | Me | H | NHCH(CH$_2$OMe)$_2$ | 2,4-Cl$_2$—Ph | |
| 12 | Ic | Me | H | NHCH(Et)CH$_2$OMe | 2,4-Cl$_2$—Ph | |
| 13 | Ic | Me | H | NH-2-butyl | 2,4-Cl$_2$—Ph | |
| 14 | Ic | Me | H | OCH(Et)CH$_2$OMe | 2,4-Cl$_2$—Ph | |
| 15 | Ic | Me | H | O-3-pentyl | 2,4-Cl$_2$—Ph | |
| 16 | Ic | Me | H | O-2-pentyl | 2,4-Cl$_2$—Ph | |
| 17 | Ic | Me | H | R-2-pentyl | 2,4-Cl$_2$—Ph | |
| 18 | Ic | Me | H | S-2-pentyl | 2,4-Cl$_2$—Ph | |
| 19 | Ic | Me | H | R-2-butyl | 2,4-Cl$_2$—Ph | |
| 20 | Ic | Me | H | S-2-butyl | 2,4-Cl$_2$—Ph | |
| 21 | Ic | Me | H | CH(Et)CH$_2$OH | 2,4-Cl$_2$—Ph | |
| 22 | Ic | Me | H | CH(Et)CH$_2$OMe | 2,4-Cl$_2$—Ph | |
| 23 | Ic | Me | H | COCH$_3$ | 2,4-Cl$_2$—Ph | |
| 24 | Ic | Me | H | COEt | 2,4-Cl$_2$—Ph | |
| 25 | Ic | Me | H | CO$_2$Et | 2,4-Cl$_2$—Ph | |
| 26 | Ic | Me | H | CO-2-pentyl | 2,4-Cl$_2$—Ph | |
| 27 | Ic | Me | H | CO-3-pentyl | 2,4-Cl$_2$—Ph | |
| 28 | Ic | Me | H | CH(OH)CH$_3$ | 2,4-Cl$_2$—Ph | |
| 29 | Ic | Me | H | C(OH)Me$_2$ | 2,4-Cl$_2$—Ph | |
| 30 | Ic | Me | H | C(OH)Ph-3-pyridyl | 2,4-Cl$_2$—Ph | |
| 31 | Ic | Me | H | CH(OMe)CH$_3$ | 2,4-Cl$_2$—Ph | |
| 32 | Ic | Me | H | CH(OMe)Et | 2,4-Cl$_2$—Ph | |
| 33 | Ic | Me | H | CH(OMe)Pr | 2,4-Cl$_2$—Ph | |
| 34 | Ic | Me | H | CH(OEt)CH$_3$ | 2,4-Cl$_2$—Ph | |
| 35 | Ic | Me | H | CH(OPr)CH$_3$ | 2,4-Cl$_2$—Ph | |
| 36 | Ic | Me | H | CH(OMe)Et | 2,4-Cl$_2$—Ph | |
| 37 | Ic | Me | H | CH(OMe)Pr | 2,4-Cl$_2$—Ph | |
| 38 | Ic | Me | H | cyclobutyl | 2,4-Cl$_2$—Ph | |
| 39 | Ic | Me | H | cyclopentyl | 2,4-Cl$_2$—Ph | |
| 40 | Ic | Me | H | CH(Me)cyclobutyl | 2,4-Cl$_2$—Ph | |
| 41 | Ic | Me | H | CH(OMe)cyclobutyl | 2,4-Cl$_2$—Ph | |
| 42 | Ic | Me | H | CH(Me)cyclopropyl | 2,4-Cl$_2$—Ph | |
| 43 | Ic | Me | H | CH(OMe)cyclopropyl | 2,4-Cl$_2$—Ph | |
| 44 | Ic | Me | H | CH(Et)cyclobutyl | 2,4-Cl$_2$—Ph | |
| 45 | Ic | Me | H | CH(OEt)cyclobutyl | 2,4-Cl$_2$—Ph | |
| 46 | Ic | Me | H | CH(Et)cyclopropyl | 2,4-Cl$_2$—Ph | |
| 47 | Ic | Me | H | CH(OEt)cyclopropyl | 2,4-Cl$_2$—Ph | |
| 48 | Ic | Me | H | CH(cyclobutyl)$_2$ | 2,4-Cl$_2$—Ph | |
| 49 | Ic | Me | H | CH(cyclopropyl)$_2$ | 2,4-Cl$_2$—Ph | |
| 50 | Ic | Me | H | NHCH(CH$_2$OMe)$_2$ | 2,4,6-Me$_3$—Ph | |
| 51 | Ic | Me | H | NHCH(Et)CH$_2$OMe | 2,4,6-Me$_3$—Ph | |
| 52 | Ic | Me | H | NH-2-butyl | 2,4,6-Me$_3$—Ph | |
| 53 | Ic | Me | H | OCH(Et)CH$_2$OMe | 2,4,6-Me$_3$—Ph | |
| 54 | Ic | Me | H | O-3-pentyl | 2,4,6-Me$_3$—Ph | |
| 55 | Ic | Me | H | O-2-pentyl | 2,4,6-Me$_3$—Ph | |
| 56 | Ic | Me | H | R-2-pentyl | 2,4,6-Me$_3$—Ph | |
| 57 | Ic | Me | H | S-2-pentyl | 2,4,6-Me$_3$—Ph | |
| 58 | Ic | Me | H | R-2-butyl | 2,4,6-Me$_3$—Ph | |
| 59 | Ic | Me | H | S-2-butyl | 2,4,6-Me$_3$—Ph | |
| 60 | Ic | Me | H | 3-pentyl | 2,4,6-Me$_3$—Ph | |
| 61 | Ic | Me | H | CH(Et)CH$_2$OH | 2,4,6-Me$_3$—Ph | |
| 62 | Ic | Me | H | CH(Et)CH$_2$OMe | 2,4,6-Me$_3$—Ph | |
| 63 | Ic | Me | H | COCH$_3$ | 2,4,6-Me$_3$—Ph | |
| 64 | Ic | Me | H | COEt | 2,4,6-Me$_3$—Ph | |
| 65 | Ic | Me | H | CO$_2$Et | 2,4,6-Me$_3$—Ph | |
| 66 | Ic | Me | H | CO-2-pentyl | 2,4,6-Me$_3$—Ph | |
| 67 | Ic | Me | H | CO-3-pentyl | 2,4,6-Me$_3$—Ph | |
| 68 | Ic | Me | H | CH(OH)CH$_3$ | 2,4,6-Me$_3$—Ph | |
| 69 | Ic | Me | H | C(OH)Me$_2$ | 2,4,6-Me$_3$—Ph | |
| 70 | Ic | Me | H | C(OH)Ph-3-pyridyl | 2,4,6-Me$_3$—Ph | |
| 71 | Ic | Me | H | CH(OMe)CH$_3$ | 2,4,6-Me$_3$—Ph | |
| 72 | Ic | Me | H | CH(OMe)Et | 2,4,6-Me$_3$—Ph | |
| 73 | Ic | Me | H | CH(OMe)Pr | 2,4,6-Me$_3$—Ph | |
| 74 | Ic | Me | H | CH(OEt)CH$_3$ | 2,4,6-Me$_3$—Ph | |
| 75 | Ic | Me | H | CH(OPr)CH$_3$ | 2,4,6-Me$_3$—Ph | |
| 76 | Ic | Me | H | CH(OMe)Et | 2,4,6-Me$_3$—Ph | |
| 77 | Ic | Me | H | CH(OMe)Pr | 2,4,6-Me$_3$—Ph | |
| 78 | Ic | Me | H | cyclobutyl | 2,4,6-Me$_3$—Ph | |
| 79 | Ic | Me | H | cyclopentyl | 2,4,6-Me$_3$—Ph | |
| 80 | Ic | Me | H | CH(Me)cyclobutyl | 2,4,6-Me$_3$—Ph | |
| 81 | Ic | Me | H | CH(OMe)cyclobutyl | 2,4,6-Me$_3$—Ph | |
| 82 | Ic | Me | H | CH(Me)cyclopropyl | 2,4,6-Me$_3$—Ph | |
| 83 | Ic | Me | H | CH(OMe)cyclopropyl | 2,4,6-Me$_3$—Ph | |
| 84 | Ic | Me | H | CH(Et)cyclobutyl | 2,4,6-Me$_3$—Ph | |
| 85 | Ic | Me | H | CH(OEt)cyclobutyl | 2,4,6-Me$_3$—Ph | |

TABLE 1-continued

| | | | | | | |
|---|---|---|---|---|---|---|
| 86 | Ic | Me | H | CH(Et)cyclopropyl | 2,4,6-Me$_3$—Ph | |
| 87 | Ic | Me | H | CH(OEt)cyclopropyl | 2,4,6-Me$_3$—Ph | |
| 88 | Ic | Me | H | CH(cyclobutyl)$_2$ | 2,4,6-Me$_3$—Ph | |
| 89 | Ic | Me | H | CH(cyclopropyl)$_2$ | 2,4,6-Me$_3$—Ph | |
| 90 | Ic | Me | H | NHCH(CH$_2$OMe)$_2$ | 2-Me-4-MeO—Ph | |
| 91 | Ic | Me | H | NHCH(Et)CH$_2$OMe | 2-Me-4-MeO—Ph | |
| 92 | Ic | Me | H | NH-2-butyl | 2-Me-4-MeO—Ph | |
| 93 | Ic | Me | H | OCH(Et)CH$_2$OMe | 2-Me-4-MeO—Ph | |
| 94 | Ic | Me | H | O-3-pentyl | 2-Me-4-MeO—Ph | |
| 95 | Ic | Me | H | O-2-pentyl | 2-Me-4-MeO—Ph | |
| 96 | Ic | Me | H | R-2-pentyl | 2-Me-4-MeO—Ph | |
| 97 | Ic | Me | H | S-2-pentyl | 2-Me-4-MeO—Ph | |
| 98 | Ic | Me | H | R-2-butyl | 2-Me-4-MeO—Ph | |
| 99 | Ic | Me | H | S-2-butyl | 2-Me-4-MeO—Ph | |
| 100 | Ic | Me | H | 3-pentyl | 2-Me-4-MeO—Ph | |
| 101 | Ic | Me | H | CH(Et)CH$_2$OH | 2-Me-4-MeO—Ph | |
| 102 | Ic | Me | H | CH(Et)CH$_2$OMe | 2-Me-4-MeO—Ph | |
| 103 | Ic | Me | H | COCH$_3$ | 2-Me-4-MeO—Ph | |
| 104 | Ic | Me | H | COEt | 2-Me-4-MeO—Ph | |
| 105 | Ic | Me | H | CO$_2$Et | 2-Me-4-MeO—Ph | |
| 106 | Ic | Me | H | CO-2-pentyl | 2-Me-4-MeO—Ph | |
| 107 | Ic | Me | H | CO-3-pentyl | 2-Me-4-MeO—Ph | |
| 108 | Ic | Me | H | CH(OH)CH$_3$ | 2-Me-4-MeO—Ph | |
| 109 | Ic | Me | H | C(OH)Me$_2$ | 2-Me-4-MeO—Ph | |
| 110 | Ic | Me | H | C(OH)Ph-3-pyridyl | 2-Me-4-MeO—Ph | |
| 111 | Ic | Me | H | CH(OMe)CH$_3$ | 2-Me-4-MeO—Ph | |
| 112 | Ic | Me | H | CH(OMe)Et | 2-Me-4-MeO—Ph | |
| 113 | Ic | Me | H | CH(OMe)Pr | 2-Me-4-MeO—Ph | |
| 114 | Ic | Me | H | CH(OEt)CH$_3$ | 2-Me-4-MeO—Ph | |
| 115 | Ic | Me | H | CH(OPr)CH$_3$ | 2-Me-4-MeO—Ph | |
| 116 | Ic | Me | H | CH(OMe)Et | 2-Me-4-MeO—Ph | |
| 117 | Ic | Me | H | CH(OMe)Pr | 2-Me-4-MeO—Ph | |
| 118 | Ic | Me | H | cyclobutyl | 2-Me-4-MeO—Ph | |
| 119 | Ic | Me | H | cyclopentyl | 2-Me-4-MeO—Ph | |
| 120 | Ic | Me | H | CH(Me)cyclobutyl | 2-Me-4-MeO—Ph | |
| 121 | Ic | Me | H | CH(OMe)cyclobutyl | 2-Me-4-MeO—Ph | |
| 122 | Ic | Me | H | CH(Me)cyclopropyl | 2-Me-4-MeO—Ph | |
| 123 | Ic | Me | H | CH(OMe)cyclopropyl | 2-Me-4-MeO—Ph | |
| 124 | Ic | Me | H | CH(Et)cyclobutyl | 2-Me-4-MeO—Ph | |
| 125 | Ic | Me | H | CH(OEt)cyclobutyl | 2-Me-4-MeO—Ph | |
| 126 | Ic | Me | H | CH(Et)cyclopropyl | 2-Me-4-MeO—Ph | |
| 127 | Ic | Me | H | CH(OEt)cyclopropyl | 2-Me-4-MeO—Ph | |
| 128 | Ic | Me | H | CH(cyclobutyl)$_2$ | 2-Me-4-MeO—Ph | |
| 129 | Ic | Me | H | CH(cyclopropyl)$_2$ | 2-Me-4-MeO—Ph | |
| 130 | Ic | Me | H | NHCH(CH$_2$OMe)$_2$ | 2-Cl-4-MeO—Ph | |
| 131 | Ic | Me | H | NHCH(Et)CH$_2$OMe | 2-Cl-4-MeO—Ph | |
| 132 | Ic | Me | H | NH-2-butyl | 2-Cl-4-MeO—Ph | |
| 133 | Ic | Me | H | OCH(Et)CH$_2$OMe | 2-Cl-4-MeO—Ph | |
| 134 | Ic | Me | H | O-3-pentyl | 2-Cl-4-MeO—Ph | |
| 135 | Ic | Me | H | O-2-pentyl | 2-Cl-4-MeO—Ph | |
| 136 | Ic | Me | H | R-2-pentyl | 2-Cl-4-MeO—Ph | |
| 137 | Ic | Me | H | S-2-pentyl | 2-Cl-4-MeO—Ph | |
| 138 | Ic | Me | H | R-2-butyl | 2-Cl-4-MeO—Ph | |
| 139 | Ic | Me | H | S-2-butyl | 2-Cl-4-MeO—Ph | |
| 140 | Ic | Me | H | 3-pentyl | 2-Cl-4-MeO—Ph | amorph |
| 141 | Ic | Me | H | CH(Et)CH$_2$OH | 2-Cl-4-MeO—Ph | |
| 142 | Ic | Me | H | CH(Et)CH$_2$OMe | 2-Cl-4-MeO—Ph | |
| 143 | Ic | Me | H | COCH$_3$ | 2-Cl-4-MeO—Ph | |
| 144 | Ic | Me | H | COEt | 2-Cl-4-MeO—Ph | |
| 145 | Ic | Me | H | CO$_2$Et | 2-Cl-4-MeO—Ph | |
| 146 | Ic | Me | H | CO-2-pentyl | 2-Cl-4-MeO—Ph | |
| 147 | Ic | Me | H | CO-3-pentyl | 2-Cl-4-MeO—Ph | |
| 148 | Ic | Me | H | CH(OH)CH$_3$ | 2-Cl-4-MeO—Ph | |
| 149 | Ic | Me | H | C(OH)Me$_2$ | 2-Cl-4-MeO—Ph | |
| 150 | Ic | Me | H | C(OH)Ph-3-pyridyl | 2-Cl-4-MeO—Ph | |
| 151 | Ic | Me | H | CH(OMe)CH$_3$ | 2-Cl-4-MeO—Ph | |
| 152 | Ic | Me | H | CH(OMe)Et | 2-Cl-4-MeO—Ph | |
| 153 | Ic | Me | H | CH(OMe)Pr | 2-Cl-4-MeO—Ph | |
| 154 | Ic | Me | H | CH(OEt)CH$_3$ | 2-Cl-4-MeO—Ph | |
| 155 | Ic | Me | H | CH(OPr)CH$_3$ | 2-Cl-4-MeO—Ph | |
| 156 | Ic | Me | H | CH(OMe)Et | 2-Cl-4-MeO—Ph | |
| 157 | Ic | Me | H | CH(OMe)Pr | 2-Cl-4-MeO—Ph | |
| 158 | Ic | Me | H | cyclobutyl | 2-Cl-4-MeO—Ph | |
| 159 | Ic | Me | H | cyclopentyl | 2-Cl-4-MeO—Ph | |
| 160 | Ic | Me | H | CH(Me)cyclobutyl | 2-Cl-4-MeO—Ph | |
| 161 | Ic | Me | H | CH(OMe)cyclobutyl | 2-Cl-4-MeO—Ph | |
| 162 | Ic | Me | H | CH(Me)cyclopropyl | 2-Cl-4-MeO—Ph | |
| 163 | Ic | Me | H | CH(OMe)cyclopropyl | 2-Cl-4-MeO—Ph | |
| 164 | Ic | Me | H | CH(Et)cyclobutyl | 2-Cl-4-MeO—Ph | |

TABLE 1-continued

| | | | | | | |
|---|---|---|---|---|---|---|
| 165 | Ic | Me | H | CH(OEt)cyclobutyl | 2-Cl-4-MeO—Ph | |
| 166 | Ic | Me | H | CH(Et)cyclopropyl | 2-Cl-4-MeO—Ph | |
| 167 | Ic | Me | H | CH(OEt)cyclopropyl | 2-Cl-4-MeO—Ph | |
| 168 | Ic | Me | H | CH(cyclobutyl)$_2$ | 2-Cl-4-MeO—Ph | |
| 169 | Ic | Me | H | CH(cyclopropyl)$_2$ | 2-Cl-4-MeO—Ph | |
| 170 | Ic | Me | H | R-2-pentyl | 2-Me-6-MeO-pyrid-3-yl | |
| 171 | Ic | Me | H | S-2-pentyl | 2-Me-6-MeO-pyrid-3-yl | |
| 172 | Ic | Me | H | R-2-butyl | 2-Me-6-MeO-pyrid-3-yl | |
| 173 | Ic | Me | H | S-2-butyl | 2-Me-6-MeO-pyrid-3-yl | |
| 174 | Ic | Me | H | 3-pentyl | 2-Me-6-MeO-pyrid-3-yl | |
| 175 | Ic | Me | H | CH(Et)CH$_2$OH | 2-Me-6-MeO-pyrid-3-yl | |
| 176 | Ic | Me | H | CH(Et)CH$_2$OMe | 2-Me-6-MeO-pyrid-3-yl | |
| 177 | Id | Me | H | NHCH(CH$_2$OMe)$_2$ | 2,4-Cl$_2$—Ph | |
| 178 | Id | Me | H | NHCH(Et)CH$_2$OMe | 2,4-Cl$_2$—Ph | |
| 179 | Id | Me | H | NH-2-butyl | 2,4-Cl$_2$—Ph | |
| 180 | Id | Me | H | OCH(Et)CH$_2$OMe | 2,4-Cl$_2$—Ph | |
| 181 | Id | Me | H | O-3-pentyl | 2,4-Cl$_2$—Ph | |
| 182 | Id | Me | H | O-2-pentyl | 2,4-Cl$_2$—Ph | |
| 183 | Id | Me | H | R-2-pentyl | 2,4-Cl$_2$—Ph | |
| 184 | Id | Me | H | S-2-pentyl | 2,4-Cl$_2$—Ph | |
| 185 | Id | Me | H | R-2-butyl | 2,4-Cl$_2$—Ph | |
| 186 | Id | Me | H | S-2-butyl | 2,4-Cl$_2$—Ph | |
| 187 | Id | Me | H | CH(Et)CH$_2$OH | 2,4-Cl$_2$—Ph | |
| 189 | Id | Me | H | CH(Et)CH$_2$OMe | 2,4-Cl$_2$—Ph | |
| 190 | Id | Me | H | COCH$_3$ | 2,4-Cl$_2$—Ph | |
| 191 | Id | Me | H | COEt | 2,4-Cl$_2$—Ph | |
| 192 | Id | Me | H | CO$_2$Et | 2,4-Cl$_2$—Ph | |
| 193 | Id | Me | H | CO-2-pentyl | 2,4-Cl$_2$—Ph | |
| 194 | Id | Me | H | CO-3-pentyl | 2,4-Cl$_2$—Ph | |
| 195 | Id | Me | H | CH(OH)CH$_3$ | 2,4-Cl$_2$—Ph | |
| 196 | Id | Me | H | C(OH)Me$_2$ | 2,4-Cl$_2$—Ph | |
| 197 | Id | Me | H | C(OH)Ph-3-pyridyl | 2,4-Cl$_2$—Ph | |
| 198 | Id | Me | H | CH(OMe)CH$_3$ | 2,4-Cl$_2$—Ph | |
| 199 | Id | Me | H | CH(OMe)Et | 2,4-Cl$_2$—Ph | |
| 200 | Id | Me | H | CH(OMe)Pr | 2,4-Cl$_2$—Ph | |
| 201 | Id | Me | H | CH(OEt)CH$_3$ | 2,4-Cl$_2$—Ph | |
| 202 | Id | Me | H | CH(OPr)CH$_3$ | 2,4-Cl$_2$—Ph | |
| 203 | Id | Me | H | CH(OMe)Et | 2,4-Cl$_2$—Ph | |
| 204 | Id | Me | H | CH(OMe)Pr | 2,4-Cl$_2$—Ph | |
| 205 | Id | Me | H | cyclobutyl | 2,4-Cl$_2$—Ph | |
| 206 | Id | Me | H | cyclopentyl | 2,4-Cl$_2$—Ph | |
| 207 | Id | Me | H | CH(Me)cyclobutyl | 2,4-Cl$_2$—Ph | |
| 208 | Id | Me | H | CH(OMe)cyclobutyl | 2,4-Cl$_2$—Ph | |
| 209 | Id | Me | H | CH(Me)cyclopropyl | 2,4-Cl$_2$—Ph | |
| 210 | Id | Me | H | CH(OMe)cyclopropyl | 2,4-Cl$_2$—Ph | |
| 211 | Id | Me | H | CH(Et)cyclobutyl | 2,4-Cl$_2$—Ph | |
| 212 | Id | Me | H | CH(OEt)cyclobutyl | 2,4-Cl$_2$—Ph | |
| 213 | Id | Me | H | CH(Et)cyclopropyl | 2,4-Cl$_2$—Ph | |
| 214 | Id | Me | H | CH(OEt)cyclopropyl | 2,4-Cl$_2$—Ph | |
| 215 | Id | Me | H | CH(cyclobutyl)$_2$ | 2,4-Cl$_2$—Ph | |
| 216 | Id | Me | H | CH(cyclopropyl)$_2$ | 2,4-Cl$_2$—Ph | |
| 217 | Ic | Me | H | 3-pentyl | 2,4-Me$_2$-4-MeOPh | 80–82 |
| 218 | Ic | Me | — | 4-heptyl | 2,4-Cl$_2$—Ph | 75.5–76.5 |
| 219 | Ic | Me | — | CH(Me)cyclobutyl | 2,4-Cl$_2$—Ph | |
| 220 | Ic | Me | — | CH(CH$_2$OMe)Pr | 2,4-Cl$_2$—Ph | |
| 221 | Ic | Me | — | CH(CH$_2$CH$_2$OMe)$_2$ | 2,4-Cl$_2$—Ph | |
| 222 | Ic | Me | — | CH(CH$_2$CH$_2$OMe)Et | 2,4-Cl$_2$—Ph | |
| 223 | Ic | Me | — | CH(CH$_2$CH$_2$OMe)-cyclobutyl | 2,4-Cl$_2$—Ph | |
| 224 | Ic | Me | — | CH(CH$_2$CH$_2$OMe)3-tetrahydrofuranyl | 2,4-Cl$_2$—Ph | |
| 225 | Ic | Me | — | 3-pentyl | 2-Cl-4-OMe—Ph | |
| 226 | Ic | Me | — | CH(Me)Pr | 2-Cl-4-OMe—Ph | |
| 227 | Ic | Me | — | 4-heptyl | 2-Cl-4-OMe—Ph | |
| 228 | Ic | Me | — | CH(CH$_2$OMe)Pr | 2-Cl-4-OMe—Ph | |
| 229 | Ic | Me | — | CH(Me)cyclobutyl | 2-Cl-4-OMe—Ph | |
| 230 | Ic | Me | — | CH(Me)Pr | 2-Cl-4,5-OMe$_2$—Ph | |
| 231 | Ic | Me | — | CH(Me)cyclobutyl | 2-Cl-4,5-OMe$_2$—Ph | |
| 232 | Ic | Me | — | CH(CH$_2$CH$_2$OMe)$_2$ | 2-Cl-4,5-OMe$_2$—Ph | |
| 233 | Ic | Me | — | 4-heptyl | 2-Cl-4,5-OMe$_2$—Ph | |
| 234 | Ic | Me | — | CH(CH$_2$OMe)Pr | 2-Cl-4,5-OMe$_2$—Ph | |
| 235 | Ic | Me | — | CH(CH$_2$CH$_2$OMe)cyclobutyl | 2-Cl-4,5-OMe$_2$—Ph | |
| 236 | Ic | Me | — | CH(CH$_2$CH$_2$OMe)-3-tetrahydrofuranyl | 2-Cl-4,5-OMe$_2$—Ph | |
| 237 | Ic | Me | — | CH(Me)cyclobutyl | 2-Cl-4-OMe-5-FPh | |
| 238 | Ic | Me | — | CH(Me)Pr | 2-Cl-4-OMe-5-F—Ph | |
| 239 | Ic | Me | — | CH(CH$_2$CH$_2$OMe)$_2$ | 2-Cl-4-OMe-5-F—Ph | |
| 240 | Ic | Me | — | CH(CH$_2$CH$_2$OMe)Et | 2-Cl-4-OMe-5-F—Ph | |
| 241 | IC | Me | — | CH(CH$_2$OMe)Pr | 2-Cl-4-OMe-5-F—Ph | |
| 242 | Ic | Me | — | CH(CH$_2$CH$_2$OMe)-cyclobutyl | 2-Cl-4-OMe-5-F—Ph | |
| 243 | Ic | Me | — | CH(CH$_2$CH$_2$OMe)-3-tetrahydrofuranyl | 2-Cl-4-OMe-5-F—Ph | |
| 244 | Ic | Me | — | 3-pentyl | 2-Cl-4-OEt—Ph | |

TABLE 1-continued

| | | | | | | |
|---|---|---|---|---|---|---|
| 245 | Ic | Me | — | CH(Me)Pr | 2-Cl-4-OEt—Ph | |
| 246 | Ic | Me | — | 4-heptyl | 2-Cl-4-OEt—Ph | 85.5–86.5 |
| 247 | Ic | Me | — | CH(Me)cyclobutyl | 2,4-OMe$_2$—Ph | |
| 248 | Ic | Me | — | 3-pentyl | 2,4-OMe$_2$—Ph | |
| 249 | Ic | Me | — | 4-heptyl | 2,4-OMe$_2$—Ph | 87–88 |
| 250 | Ic | Me | — | 3-pentyl | 2-Me-4-Cl—Ph | |
| 251 | Ic | Me | — | 3-pentyl | 4-OMe—Ph | |
| 252 | Ic | Me | — | 3-pentyl | 4-Cl—Ph | |
| 253 | Ic | Me | — | 3-pentyl | 2,5-Me$_2$-4-OMe—Ph | 80–82 |
| 254 | Ic | Me | — | 3-pentyl | 2-Cl-4-SO$_2$Me—Ph | |
| 255 | Ic | Me | — | 3-pentyl | 2-Me-4-NMe$_2$—Ph | |
| 256 | Ic | Me | — | 3-pentyl | 2-Cl-4-NMe$_2$—Ph | |
| 257 | Ic | Me | — | 3-pentyl | 2-CF$_3$-4-F—Ph | |
| 258 | Ic | Me | — | 3-pentyl | 2-OMe-4-Me—Ph | |
| 259 | Ic | Me | — | CH(Me)Pr | 2-OH-4-OMe—Ph | |
| 260 | Ic | Me | — | CH(Me)Pr | 2-Me-4-OMe-5-F—Ph | |
| 261 | Id | Me | — | 3-pentyl | 2,4-Cl$_2$—Ph | |
| 262 | Id | Me | — | 3-pentyl | 2-Cl-4,5-OMe$_2$—Ph | |

TABLE 1a

| Ex. | Formula | R$^5$ | R$^4$ | R$^2$ | R$^3$ | mp (° C.) |
|---|---|---|---|---|---|---|
| 263 | | Me | — | 3-pentyl | 2-Cl-4,5-OMe$_2$—Ph | 249–250 |

In addition to examples 1–10, additional examples 11–248 and additional examples having the following R$^4$ (or R$^5$), R$^2$ and R$^3$ were or may readily be prepared according to the procedures described herein.

The preferred groups for R$^5$ in the compounds of formula Ic and Id are methyl (Me). For R$^2$, in compounds of formula Ic and Id having R$^5$ as Me (or C$_2$–C$_6$alkyl), the preferred groups include 3-pentyl, NEt$_2$, butyl, NHCH(CH$_2$OMe)$_2$, NHCH(CH$_2$OEt)$_2$, NHCH(Et)CH$_2$OMe, NH-3-heptyl, NH-3-pentyl, NH-2-butyl, NH-3-hexyl, NHCH(CH$_2$Ph)CH$_2$OMe, NHCH(Et)CH$_2$CH$_2$OMe, NH-cyclobutyl, NH-cyclopentyl, NEtPr, NEtBu, NMePr, NMePh, Npr$_2$, NPr(CH$_2$-c-C$_3$H$_5$), N(CH$_2$CH$_2$OMe)$_2$, morpholino, N(CH$_2$Ph)CH$_2$CH$_2$OMe, N(Me)CH$_2$CH$_2$OMe, N(Et)CH$_2$CH$_2$OMe, N(CH$_2$-c-C$_3$H$_5$)CH$_2$CH$_2$OMe, N(CH$_2$-c-C$_3$H$_5$)Pr, N(CH$_2$-c-C$_3$H$_5$)Et, OEt, OCH(Et)CH$_2$OMe, OCH(Et)CH$_2$CH$_2$OMe, OCH(Me)CH$_2$CH$_2$OMe, O-3-pentyl, O-2-pentyl, S-3-pentyl, S-2-pentyl, SEt, S(O)Et, SO$_2$Et, S-3-pentyl, S(O)-3-pentyl, SO$_2$-3-pentyl, S-2-pentyl, S(O)-2-pentyl, SO$_2$-2-pentyl, CH(CO$_2$Et)$_2$, C(Et)(CO$_2$Et)$_2$, CH(Et)CH$_2$OH, CH(Et)CH$_2$OMe, CH(Et)CH$_2$CH$_2$OMe, CONMe$_2$, COCH$_3$, COEt, COPr, CO-2-pentyl, CO-3-pentyl, CH(OH)CH$_3$, C(OH)Me$_2$, C(OH)Ph-3-pyridyl, CH(OMe)CH$_3$, CH(OMe)Et, CH(OMe)Pr, CH(OEt)CH$_3$, CH(OPr)CH$_3$, 2-pentyl, 2-butyl, cyclobutyl, cyclopentyl, CH(Me)cyclobutyl, CH(OMe)cyclobutyl, CH(OH)cyclobutyl, CH(Me)cyclopropyl, CH(OMe)cyclopropyl, CH(OH)cyclopropyl, CH(Et)cyclobutyl, CH(Et)cyclopropyl, CH(OMe)cyclobutyl, CH(OMe)cyclopropyl, CH(OEt)cyclobutyl, CH(OEt)cyclopropyl, CH(Me)CH$_2$-cyclobutyl, CH(OMe)CH$_2$-cyclobutyl, CH(OH)CH$_2$-cyclobutyl, CH(Me)CH$_2$-cyclopropyl, CH(OMe)CH$_2$-cyclopropyl, CH(OH)CH$_2$-cyclopropyl, CH(Et)CH$_2$-cyclobutyl, CH(Et)CH$_2$-cyclopropyl, CH(OMe)CH$_2$-cyclobutyl, CH(OMe)CH$_2$-cyclopropyl, CH(OEt)CH$_2$-cyclobutyl, CH(OEt)CH$_2$-cyclopropyl, CH(CH$_2$OMe)cyclobutyl, CH(CH$_2$OMe)cyclopropyl, CH(CH$_2$OEt)cyclobutyl, CH(CH$_2$OEt)cyclopropyl, CH(cyclobutyl)$_2$, CH(cyclopropyl)$_2$, CH(Et)CH$_2$CONMe$_2$, CH(Et)CH$_2$CH$_2$Me$_2$, CH(CH$_2$OMe)Me, CH(CH$_2$OMe)Et, CH(CH$_2$OMe)Pr, CH(CH$_2$OEt)Me, CH(CH$_2$OEt)Et, CH(CH$_2$OEt)Pr, CH(CH$_2$C≡CMe)Et, CH(CH$_2$C≡CMe)Et. The preferred groups for R$^3$ with R$^2$ and R$^5$ as defined above include 2,4-Cl$_2$—Ph, 2,4,6-Me$_3$-Ph, 2,4-Me$_2$-Ph, 2-Me-4-MeO—Ph, 2-Cl-4-MeO—Ph, 2-Cl-4,5-(MeO)$_2$—Ph, 2-Cl-4-MeO-5-F—Ph, 2-Me-4-MeO-5-F—Ph, 2,5-(Me)$_2$-4-MeO—Ph, 2-Me-4-NMe$_2$-Ph, 2-CF$_3$-4-MeO—Ph, 2-Me-4-(COMe)-Ph 2-Me-6-Me$_2$N-pyrid-3-yl, 4-Me-2-Me$_2$N-pyrid-5-yl, 2-Me-6-MeO-pyrid-3-yl, 4-Me-2-MeO-pyrid-5-yl. Each of the compounds within the independent generic variations may readily be prepared according to the procedures described in Schemes 1–3 and 5. For compounds of formulas Ie and If, in addition to example 10 in Table 1, the above variables for Ic and Id may be used in the compounds of formulas Ie and If except that R$^5$ groups are used as the R$^4$ variables. The following compounds may be prepared as the preferred embodiments wherein R$^4$ is selected from H, OCH$_3$CH$_3$ and C$_2$H$_5$; R$^2$ is selected from CH(C$_2$H$_5$)$_2$, CH(c-C$_3$H$_5$)$_2$, CHC$_2$H$_5$(c-C$_3$H$_5$), CH(C$_2$H$_5$)$_2$, CH(c-C$_3$H$_5$)$_2$; and R$^3$ is selected from 2,4-Cl$_2$—Ph, 2-Cl-4-CH$_3$O—Ph, 2,4,6-(CH$_3$)$_3$—Ph, 2-Cl-4-CF$_3$—Ph and 2-(CH$_3$)$_2$N-4-CH$_3$-pyridin-5-yl. In addition, the methoxy group or the ethyl group in the R$^1$ position also preferrably includes CH$_3$ and H. Each of the compounds within the independent generic variations may readily be prepared according to the procedure described in Scheme 4. Compounds of formula IIa and IIb are readily prepared according to the procedure described in Scheme 6. These compounds also preferrably have the variables shown in the examples and described above.

UTILITY

CRF-R1 Receptor Binding Assay for the Evaluation of Biological Activity

Radioligand Binding Experiments

Compounds of the invention were tested for in vitro activity as CRF receptor antagonists. The tests described below demonstrated that the examples tested had K$_i$s of 10,000 nM or less and are thus useful as CRF receptor antagonists. Preferred antagonists have or will have a K$_i$ of 1,000 nM or less. Radioligand binding experiments were performed with membranes from rat frontal cortex to determine binding affinities ($K_i$'s) of test compounds for the rat $CRH_1$ receptor using a modified version of methods described earlier (see E. B. DeSouza, J. Neurosci, 7:88, 1987). Rat cortex was homogenized in tissue buffer (containing 50 mM HEPES, 10 mM $MgCl_2$, 2 mM EGTA, and 1 µg/ml each of aprotonin, leupeptin, and pepstatin, pH 7.0@23° C.) using a Brinkman Polytron (PT-10, setting 6 for 10 sec). The homogenate was centrifuged at 48,000×g for 12 min and the resulting pellet was washed by two sequential re-suspension and centrifugation steps. The final pellet was suspended to tissue buffer to a working concentration of 0.1 mg/ml protein. Protein determinations were made using the bicinchoninic acid (BCA) assay (Pierce, Rockford, Ill.) with bovine serum albumin as the standard.

All test compounds were prepared in assay buffer, which was identical to the tissue buffer except for the inclusion of 0.15 mM bacitracin and 0.1% w/v ovalbumin. Binding assay were conducted in disposable polypropylene 96-well plates (Costar Corp., Cambridge, Mass.) and initiated by the addition of 100 µl membrane homogenate (containing 40–60 µg protein) to 200 µl of assay buffer containing radioligands (150 pM, final concentration, [$^{125}$I] tyro° ovine CRH; New England Nuclear, Mass.) and competing test compounds. Specific binding was determined in the presence of 10 µM α-helical CRH. Competition experiments were conducted using 12 concentrations of ligand (ranging from $1\times10^{31\ 11}$ to $1\times10^{-5}$ M). The reactions mixtures were incubated to equilibrium for 2 hr at 23° C. and terminated by rapid filtration using a cell harvester (Inotech Biosystems Inc., Lansing Mich.) over GFF glass-fibers (pre-soaked in 0.3% v/v polyethyleneimine). Filters were rapidly washed 3× with 0.3 ml cold wash buffer (PBS, pH 7.0, containing 0.01% Triton X-100), dried, and counted in a gamma counter at 80% efficiency.

Binding affinities ($K_i$'s) of ligands for the $CRH_1$ receptor were calculated using the iterative nonlinear regression curve-fitting programs (LIGAND) of Munson and Rodbard (Anal. Biochem. 1980, 107, 220–239) or Prism (GraphPad Prism, San Diego, Calif.). Data were best-fit by the one-site/state competition equation.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions are initiated by the addition of 1 mM ATP/$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990).

Compounds may be Tested in Any Species of Rodent or Small Mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease. The preferred indication and use for the compounds and compositions of the invention is in the treatment of depression or anxiety.

What is claimed is:

1. A compound of formula I:

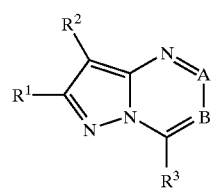

(I)

or a stereoisomer or pharmaceutically acceptable salt thereof, wherein:

A is N;

B is $CR^4$ $R^1$ is independently selected from the group consisting of

H, halogen,

CN, $C_{1-6}$ alkyl, $C_{2-10}$ alkenyl, $C_{2-10}$ alkynyl, $C_{3-6}$ cycloalkyl, $C_{1-6}$ alkyloxy, $C_{1-6}$ alkylS(O)$_n$, —$NR^{1a}R^{1b}$ wherein $R^{1a}$ and $R^{1b}$ are independently selected from H, $C_{1-4}$ alkyl, $C_{3-8}$ cycloalkyl, —C(O) $C_{1-4}$alkyl, $C_{1-6}$ alkyl$NR^{1a}R^{1b}$, $NR^{1a}COR^{1b}$, —C(O)$NR^{1a}R^{1b}$, —O—C(O)$C_{1-4}$alkyl, and —$XR^{1c}$ wherein $R^{1c}$ is selected from H or —$C_{1-4}$ alkylaryl; and X is selected from O or S(O)$_n$, wherein $R^1$ is substituted with 0–6 substituents selected from halogen, $C_{1-4}$ alkyl, $C_{3-8}$ cycloalkyl, $C_{1-6}$ alkyloxy, $C_{1-4}$ haloalkyl, $C_{1-4}$ alkylamino, $C_{2-8}$ dialkylamino, $C_{1-4}$ alkylthio, $C_{1-4}$ alkylsulfinyl and $C_{1-4}$ alkylsulfonyl;

$R^2$ is selected from the group consisting of H, $OR^7$, SH, $NR^6R^7$, $C(OH)R^6R^{6a}$, $C(OR^7)R^6R^{6a}$, $S(O)_nR^{13}$, $COR^7$, $CO_2R^7$, $CHR^6(OR^7)R^{6a}$, $OC(O)R^{13}$, NO, $NO_2$, $NR^6C(O)R^7$, $N(COR^7)_2$, $NR^8CONR^6R^7$, $NR^6CO_2R^7$, $C_{1-10}$ alkyl, $C_{2-10}$ alkenyl, $C_{2-10}$ alkynyl, $C_{3-8}$ cycloalkyl, $C_{3-6}$ cycloalkyl $C_{1-6}$ alkyl, $C_{1-10}$ alkyloxy, $C_{1-10}$ alkyloxy$C_{1-10}$ alkyl, —$SO_2$—$C_{1-10}$alkyl —$SO_2R^{2a}$ wherein $R^{2a}$ is aryl, —$SO_2R^{2b}$ wherein $R^{2b}$ is heteroaryl, —$NR^{2c}R^{2d}$ wherein $R^{2c}$ and $R^{2d}$ are independently selected from H, $C_{1-8}$ alkyl, $S(O)_nC_{1-4}$alkyl, $C(O)NR^{2c}R^{2d}$, $CO_2C_{1-4}$alkyl, $C_{3-8}$ cycloalkyl, $C_{1-6}$ alkyloxy$C_{1-6}$ alkyl, and —C(O)$C_{1-4}$alkyl, -halogen,

—CN,

—C(O)-L wherein L is selected from H, $NR^{2c}R^{2d}$, $C_{1-6}$ alkyl or $OC_{1-4}$ alkyl, $O(CH_2)_mOR$ wherein R is $C_{1-3}$ alkyl, $O(CH_2)_m$—$NR^{2c}R^{2d}$, OH, C(O)OC$_{1-6}$alkyl or aryl or heteroaryl wherein m is 1–4; and —OC(O)-M wherein M is selected from $C_{1-4}$ alkyl, $C_{1-4}$ haloalkyl, $C_{2-8}$ alkoxyalkyl, $C_{3-6}$cycloalkyl, $C_{4-12}$ cycloalkylalkyl, aryl, $C_{1-6}$ alkylaryl, heteroaryl, and $C_{1-6}$ alkylheteroaryl;

n is 0, 1 or 2; and wherein $R^2$ is substituted with 0–3 substituents independently selected from R', R", R'" wherein R', R" and R'" are independently selected from $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{2-6}$ alkynyl, $C_{1-6}$ alkyloxy, and hydroxy, or $R^2$ is substituted with 0–3 substituents independently selected from:

halogen,

—CN,

—$S(O)_nR^{2e}$ wherein $R^{2e}$ is selected from $C_{1-4}$ alkyl, $C_{1-4}$ haloalkyl, $C_{1-4}$ alkyloxy $C_{1-4}$ alkyl, and $C_{3-6}$ cycloalkyl;

—$COR^{2f}$ wherein $R^{2f}$ is selected from H, $C_{1-4}$ alkyl, $C_{1-4}$ haloalkyl, $C_{1-4}$ alkyloxy $C_{1-4}$ alkyl, $C_{3-6}$ cycloalkyl, and $C_{3-6}$ cycloalkyl $C_{1-4}$alkyl;

—$CO_2R^{2f}$,

—$NR^{2g}COR^{2f}$ wherein $R^{2g}$ is selected from H, $C_{1-6}$ alkyl, $C_{3-7}$ cycloalkyl, and $C_{3-6}$ cycloalkyl $C_{1-6}$ alkyl;

—$N(COR^{2f})_2$,

—$NR^{2g}CONR^{2f}R^{2h}$, wherein $R^{2h}$ is selected from H, $C_{1-6}$ alkyl, $C_{1-4}$ haloalkyl, $C_{1-4}$ alkoxy $C_{1-4}$ alkyl, $C_{3-6}$ cycloalkyl and $C_{3-6}$ cycloalkyl$C_{1-6}$ alkyl;

—NR$^{2g}$CO$_2$R$^{2e}$,
—CONR$^{2g}$R$^{2h}$,
1-morpholinyl,
1-piperidinyl,
1-piperazinyl,
and
C$_{3-8}$ cycloalkyl wherein 0–1 carbon atoms in the C$_{4-8}$ cycloalkyl is replaced by a group selected from —O—, —S(O)$_n$—, —NR$^{2g}$—, —NCO$_2$R$^{2e}$, —NCOR$^{2e}$, and —NSO$_2$R$^{2e}$; and wherein N$^4$ in 1-piperazinyl is substituted with 0–1 substituents selected from R$^{2g}$, CO$_2$R$^{2e}$, COR$^{2e}$ and SO$_2$R$^{2e}$; or the group R$^{2i}$, R$^{2j}$, R$^{2k}$, C$_{1-6}$ alkyl, C$_{2-8}$ alkenyl, C$_{2-8}$ alkynyl, Br, Cl, F, I, C$_{1-4}$ haloalkyl, —OR$^{2g}$, —NR$^{2g}$R$^{2h}$, —C$_{1-6}$ alkyl-OR$^{2g}$, or C$_{3-8}$ cycloalkyl which is substituted with 0–1 R$^{21}$ and in which 0–1 carbons of C$_{4-8}$ cycloalkyl is replaced by —O—, wherein R$^{2i}$ is selected from aryl wherein aryl is selected from phenyl, naphthyl, indanyl and indenyl, each R$^{2i}$ being substituted with 0–1 OR$^{2m}$ and 0–5 substituents independently selected from the group C$_{1-6}$ alkyl, C$_{3-6}$ cycloalkyl, Br, Cl, F, I, C$_{1-4}$ haloalkyl, —CN, nitro, —SH, —S(O)$_n$R$^{2n}$, —COR$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2n}$, —NR$^{2o}$R$^{2p}$ and —CONR$^{2o}$R$^{2p}$;

R$^{2j}$ is selected from heteroaryl wherein heteroaryl is selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;

R$^{2k}$ is heterocyclyl which is a saturated or partially saturated heteroaryl as defined for R$^{2j}$, each heterocyclyl being substituted on 0–4 carbon atoms with a substituent independently selected from the group C$_{1-6}$ alkyl, C$_{3-6}$ cycloalkyl, Br, Cl, F, I, C$_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CONR$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;

wherein

R$^{21}$ is H, C$_{1-4}$ alkyl, C$_{3-6}$ cycloalky-C$_{1-4}$ alkyl or C$_{3-8}$ cycloalkyl;

R$^{2m}$ is H, C$_{1-6}$ alkyl, C$_{3-6}$ cycloalkyl C$_{1-6}$ alkyl, C$_{1-2}$ alkyloxy C$_{1-2}$ alkyl, C$_{1-4}$ haloalkyl, R$^{2q}$S(O)$_n$—C$_{1-4}$ alkyl or R$^{2r}$R$^{2s}$N—C$_{2-4}$ alkyl;

R$^{2n}$ is H, C$_{1-6}$ alkyl, C$_{3-10}$ cycloalkyl, C$_{3-6}$ cycloalkyl-C$_{1-6}$ alkyl, C$_{1-2}$ alkyloxy C$_{1-2}$ alkyl, or C$_{1-4}$ haloalkyl;

R$^{2o}$ and R$^{2p}$ are independently selected at each occurrence from H, C$_{1-6}$ alkyl, C$_{3-10}$ cycloalkyl, C$_{3-6}$ cycloalkyl C$_{1-6}$ alkyl and C$_{1-4}$ haloalkyl;

R$^{2q}$ is selected from C$_{1-6}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl (C$_{1-4}$ alkyl), heteroaryl and heteroaryl (C$_{1-4}$ alkyl)- and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy C$_{1-4}$ haloalkoxy, and dimethylamino;

R$^{2r}$R$^{2s}$ taken together with the N form 1-pyrrolidinyl, 1-morpholinyl, 1-piperidinyl or 1-piperazinyl wherein N$^4$ in 1-piperiazinyl is substituted with 0–1 substituents selected from the group R$^{2t}$, CO$_2$R$^{2q}$, COR$^{2q}$ and SO$_2$R$^{2q}$;

R$^{2t}$ is selected from H, C$_{1-4}$ alkyl, C$_{1-4}$ haloalkyl, C$_{1-4}$ alkoxy-C$_{1-4}$ alkyl, C$_{3-6}$ cycloalkyl, C$_{3-6}$ cycloalkyl-C$_{1-6}$ alkyl, aryl, aryl (C$_{1-4}$ alkyl)-, heteroaryl and heteroaryl (C$_{1-4}$ alkyl);

R$^3$ is an aryl or heteroaryl group attached through an unsaturated carbon atom;

aryl is selected from phenyl, naphthyl, indanyl and indenyl, each aryl being substituted with 0–5 substituents independently selected at each occurrence from C$_{1-6}$ alkyl, C$_{3-6}$ cycloalkyl, methylenedioxy, C$_{1-4}$ alkyloxy-C$_{1-4}$ alkyloxy, —OR$^{2m}$, Br, Cl, F, I, C$_{1-4}$ haloalkyl, —CN, —NO$_2$, —SH, —S(O)$_n$R$^{2n}$, —COR$^{2m}$, —CO$_2$R$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and CONR$^{2o}$R$^{2p}$;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substituted at 0–4 carbon atoms with a substituent independently selected at each occurrence from the group C$_{1-6}$ alkyl, C$_{3-6}$ cycloalkyl, Br, F, I, C$_{1-4}$ haloalkyl, —CN, NR$^{2g}$R$^{2h}$, nitro, —OR$^{2m}$, —SH, —S(O)$_n$R$^{2n}$, COR$^{2m}$, —CO$_2$R$^{2m}$, —OC(O)$^{2n}$, —NR$^{2g}$COR$^{2m}$, —N(COR$^{2m}$)$_2$, —NR$^{2g}$CONR$^{2o}$R$^{2p}$ and each heteroaryl being substituted at any nitrogen atom with 0–1 substituents selected from the group R$^{2g}$, CO$_2$R$^{3a}$, COR$^{3a}$ and SO$_2$R$^{3a}$ wherein, R$^{3a}$ is selected from the group C$_{1-6}$ alkyl, C$_{1-4}$ cycloalkyl-C$_{1-6}$ alkyl and benzyl, each benzyl being substituted on the aryl moiety with 0–1 substituents selected from the group C$_{1-4}$ alkyl, Br, Cl, F, I, C$_{1-4}$ haloalkyl, nitro, C$_{1-4}$ alkoxy, C$_{1-4}$ haloalkoxy, and dimethylamino;

R$^4$ is selected from H, Br, Cl, F, I, —CN, C$_{1-6}$ alkyl, C$_{2-6}$ alkenyl, C$_{2-6}$ alkynyl, C$_{3-8}$ cycloalkyl, C$_{1-6}$ alkyloxy, C$_{1-6}$ alkylthio, C$_{1-6}$ alkylsulfinyl, C$_{1-6}$ alkylsulfonyl, amino, C$_{1-4}$ alkylamino, (C$_{1-4}$ alkyl)$_2$ amino and phenyl, each phenyl is substituted with 0–3 groups selected from the group consisting of C$_{1-7}$ alkyl, C$_{3-8}$ cycloalkyl, Br, Cl, F, I, —C(O)H, C$_{1-4}$ haloalkyl, nitro, C$_{1-4}$ alkoxy, C$_{1-4}$ haloalkoxy, C$_{1-4}$ alkylthio, C$_{1-4}$ alkylsulfinyl, C$_{1-4}$ alkylsulfonyl, C$_{1-6}$ alkylamino and (C$_{1-4}$ alkyl)$_2$ amino and wherein R$^4$ non-phenyl groups may be substituted with 0–5 substituents selected from OH, halogen, —C(O)H, —OC$_{1-6}$-alkyl, C$_{1-6}$ haloalkyl, C$_{1-6}$ alkyl, C$_{3-7}$ c-alkyl, and C$_{1-6}$ alkyl(OH)$_n$CO$_2$R, wherein R is H or C$_{1-6}$ alkyl, or C$_{1-6}$ alkyl(OH)$_n$, wherein n is 0–3;

$R^6$, $R^{6a}$ and $R^7$ are independently selected from: H, $C_{1-10}$ alkyl, $C_{3-10}$ cycloalkyl, $C_{3-10}$ alkenyl, $C_{3-10}$ alkynyl, $C_{1-10}$ haloalkyl, $C_{2-8}$ alkoxyalkyl, $C_{4-12}$ cycloalkylalkyl, $C_{5-10}$ cycloalkenyl, and $C_{6-14}$ cycloalkenylalkyl;

$R^6$, $R^{6a}$ and $R^7$ are substituted with 0–6 substituents independently selected from halogen, $C_{1-4}$ alkyl, $C_{3-8}$ cycloalkyl, $C_{1-6}$ alkyloxy and $C_{1-4}$ haloalkyl;

with the proviso that when $R^1$ is H, amino, or acetamido, $R^2$ is H, and $R^3$ is unsubstituted phenyl, $R^4$ is not phenyl.

2. A compound of formula I:

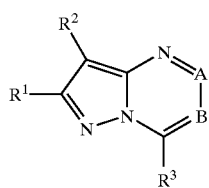

(I)

or a stereoisomer or pharmaceutically acceptable salt thereof, wherein:

A is N;

B is $CR^4$;

$R^1$ is independently selected from the group consisting of

H, halogen,

CN, $C_{1-6}$ alkyl, $C_{2-10}$ alkenyl, $C_{2-10}$ alkynyl, $C_{3-6}$ cycloalkyl, $C_{1-6}$ alkyloxy, $C_{1-6}$ alkylS(O)$_n$, —$NR^{1a}R^{1B}$ wherein $R^{1a}$ and $R^{1b}$ are independently selected from H, $C_{1-4}$ alkyl, $C_{3-8}$ cycloalkyl, —C(O)$C_{1-4}$alkyl, $C_{1-6}$ alkyl$NR^{1a}R^{1b}$, $NR^{1a}COR^{1b}$, —C(O)$NR^{1a}R^{1b}$, —O—C(O)$C_{1-4}$alkyl, and —$XR^{1c}$ wherein $R^{1c}$ is selected from H or —$C_{1-4}$ alkylaryl;

X is selected from 0 or S(O)$_n$, wherein $R^1$ is substituted with 0–6 substituents selected from halogen, $C_{1-4}$ alkyl, $C_{3-8}$ cycloalkyl, $C_{1-6}$ alkyloxy, $C_{1-4}$ haloalkyl, $C_{1-4}$alkylamino, $C_{2-8}$ dialkylamino, $C_{1-4}$alkyloxy, $C_{1-4}$ alkylthio, $C_{1-4}$ alkylsulfinyl and $C_{1-4}$ alkylsulfonyl;

$R^2$ is selected from the group consisting of $OR^7$, SH, $NR^6R^7$, $C(OH)R^6R^{6a}$, $C(OR^7)R^6R^{6a}$, $S(O)_nR^{13}$, $COR^7$, $CO_2R^7$, $CHR^6(OR^7)R^{6a}$, $OC(O)R^{13}$, NO, $NO_2$, $NR^6C(O)R^7$, $N(COR^7)_2$, $NR^8CONR^6R^7$ and $NR^6CO_2R^7$;

or $R^2$ is selected from:

$C_{1-10}$ alkyl, $C_{2-10}$ alkenyl, $C_{2-10}$ alkynyl, $C_{3-8}$ cycloalkyl, $C_{3-6}$ cycloalkyl $C_{1-6}$ alkyl, $C_{1-10}$ alkyloxy, $C_{1-10}$ alkyloxy$C_{1-10}$ alkyl, —$SO_2$—$C_{1-10}$alkyl —$SO_2R^{2a}$ wherein $R^{2a}$ is aryl, —$SO_2R^{2b}$ wherein $R^{2b}$ is heteroaryl, —$NR^{2c}R^{2D}$ wherein $R^{2c}$ and $R^{2d}$ are independently selected from H, $C_{1-8}$ alkyl, $S(O)_nC_{1-4}$alkyl, $C(O)NR^{2c}R^{2d}$, $CO_2C_{1-4}$alkyl, $C_{3-8}$cycloalkyl, $C_{1-6}$ alkyloxy$C_{1-6}$ alkyl, —$C(O)C_{1-4}$alkyl or $R^{2c}$ and $R^{2d}$ may join to form a heterocyclic ring having 0–3 heteroatoms selected from O, N or S, —(O)-L wherein L is selected from H, $NR^{2c}R^{2d}$, and $C_{1-6}$ alkyl $O(CH_2)_mOR$ wherein R is $C_{1-3}$ alkyl, $O(CH_2)_m$—$NR^{2c}R^{2d}$, OH, $C(O)OC_{1-6}$alkyl, or aryl or heteroaryl wherein m is 1–4; and —OC(O)-M wherein M is selected from $C_{1-4}$ alkyl, $C_{1-4}$ haloalkyl, $C_{2-8}$ alkoxyalkyl, $C_{3-6}$ cycloalkyl, $C_{4-12}$ cycloalkylalkyl, aryl, $C_{1-6}$ alkylaryl, heteroaryl, and $C_{1-6}$ alkylheteroaryl;

n is 0, 1 or 2; and wherein $R^2$ is substituted with 0–3 substituents independently selected from R', R", R''' wherein R', R" and R''' are independently selected from $C_{1-6}$ alkyl, $C_{3-7}$ cycloalkyl, hydroxy$C_{1-6}$ alkyl, $C_{1-6}$ alkyloxy$C_{1-6}$ alkyl, $C_{2-6}$ alkenyl, $C_{2-6}$ alkynyl, $C_{1-6}$ alkyloxy, and hydroxy, or $R^2$ is substituted with 0–3 substituents independently selected from:

halogen,

—CN,

—$S(O)_nR^{2e}$ wherein $R^{2e}$ is selected from $C_{1-4}$alkyl, $C_{1-4}$ haloalkyl, $C_{1-4}$ alkyloxy $C_{1-4}$ alkyl, and $C_{3-6}$ cycloalkyl;

—$COR^{2f}$ wherein $R^{2f}$ is selected from H, $C_{1-4}$ alkyl, $C_{1-4}$ haloalkyl, $C_{1-4}$ alkyloxy $C_{1-4}$ alkyl, $C_{3-6}$ cycloalkyl, and $C_{3-6}$ cycloalkyl$C_{1-4}$ alkyl;

—$CO_2R^{2f}$,

—$NR^{2g}COR^{2f}$ wherein $R^{2g}$ is selected from H, $C_{1-6}$ alkyl, $C_{3-7}$ cycloalkyl, and $C_{3-6}$ cycloalkyl$C_{1-6}$ alkyl;

—$N(COR^{2f})_2$,

—$NR^{2g}CONR^{2f}R^{2h}$, wherein $R^{2h}$ is selected from H, $C_{1-6}$ alkyl, $C_{1-4}$ haloalkyl, $C_{1-4}$ alkoxy $C_{1-4}$ alkyl, $C_{3-6}$ cycloalkyl and $C_{3-6}$ cycloalkyl$C_{1-6}$ alkyl;

—$NR^{2g}CO_2R^{2e}$, $CONR^{2g}R^{2h}$, 1-morpholinyl, 1-piperidinyl, 1-piperazinyl, and $C_{3-8}$ cycloalkyl wherein 0–1 carbon atoms in the $C_{4-8}$ cycloalkyl is replaced by a group selected from —O—, —$S(O)_{n-}$ —$NR^{2g}$—, —$NCO_2R^{2e}$, —$NCOR^{2e}$, and —$NSO_2R^{2e}$; and wherein $N^4$ in 1-piperazinyl is substituted with 0–1 substituents selected from $R^{2g}$, $CO_2R^{2e}$, $COR^{2e}$ and $SO_2R^{2e}$; or the group $R^{2i}$, $R^{2j}$, $R^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$, —$NR^{2g}R^{2h}$, —$C_{1-6}$ alkyl-$OR^{2g}$, or $C_{3-8}$ cycloalkyl which is substituted with 0–1 $R^{21}$ and in which 0–1 carbons of $C_{4-8}$ cycloalkyl is replaced by —O—, wherein $R^{2i}$ is selected from aryl wherein aryl is selected from phenyl, naphthyl, indanyl and indenyl, each $R^{2i}$ being substituted with 0–1 $OR^{2m}$ and 0–5 substituents independently selected from the group $C_{1-6}$ alkyl, $C_{3-6}$ cycloalkyl, Br, Cl, F, I, $C_{1-4}$ haloalkyl, —CN, nitro, —SH, —S(O)$_n$R$^{2n}$, —COR$^{2m}$, —OC(O)R$^{2n}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2n}$, —NR$^{2o}$R$^{2p}$ and —CONR$^{2o}$R$^{2p}$;

R$^{2j}$ is selected from heteroaryl wherein heteroaryl is selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-s-oxide, 2,3-dihydro-benzothienyl-S-dioxide, indolinyl, benzoxazolin-2-onyl, benzodioxolanyl and benzodioxane, each heteroaryl being substituted on 0–4 carbon atoms with a substituent independently selected from the group $C_{1-6}$ alkyl, $C_{3-6}$ cycloalkyl, Br, Cl, F, I, $C_{1-4}$ haloalkyl, —CN, nitro, OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and —CONR$^{2o}$R$^{2p}$ and each heteroaryl being substituted on any nitrogen atom with 0–1 substituents selected from the group R$^{2g}$, CO$_2$R$^{2e}$, COR$^{2e}$ and SO$_2$R$^{2e}$;

R$^{2k}$ is heterocyclyl which is a saturated or partially saturated heteroaryl as defined for R$^{2j}$, each heterocyclyl being substituted on 0–4 carbon atoms with a substituent independently selected from the group $C_{1-6}$ alkyl, $C_{3-6}$cycloalkyl, Br, Cl, F, I, $C_{1-4}$ haloalkyl, —CN, nitro, —OR$^{2m}$, —SH, —S(O)$_n$R$^{2h}$, —COR$^{2m}$, —OC(O)R$^{2h}$, —NR$^{2g}$COR$^{2m}$, —N(COR$^{2m}$)$_2$, —NR$^{2g}$CONR$^{2o}$R$^{2p}$, NR$^{2g}$CO$_2$R$^{2h}$, —NR$^{2o}$R$^{2p}$ and —CONR$^{2o}$R$^{2p}$ and each heterocyclyl being substituted on any nitrogen atom with 0–1 substituents selected from the group R$^{2f}$, CO$_2$R$^{2e}$, COR$^{2e}$ and SO$_2$R$^{2e}$;

wherein

R$^{2l}$ is H, $C_{1-4}$ alkyl, $C_{3-6}$ cycloalky-$C_{1-4}$ alkyl or $C_{3-8}$ cycloalkyl;

R$^{2m}$ is H, $C_{1-6}$ alkyl, $C_{3-6}$ cycloalkyl $C_{1-6}$ alkyl, $C_{12}$ alkyloxy $C_{1-2}$ alkyl, $C_{1-4}$ haloalkyl, R$^{2q}$S(O)$_n$—$C_{1-4}$ alkyl or R$^{2r}$R$^{2s}$N—$C_{2-4}$ alkyl;

R$^{2n}$ is H, $C_{1-6}$ alkyl, $C_{3-10}$ cycloalkyl, $C_{3-6}$ cycloalkyl-$C_{1-6}$ alkyl, $C_{1-2}$ alkyloxy $C_{1-2}$ alkyl, or $C_{1-4}$ haloalkyl;

R$^{2o}$ and R$^{2p}$ are independently selected at each occurrence from H, $C_{1-6}$ alkyl, $C_{3-10}$ cycloalkyl, $C_{3-6}$ cycloalkyl $C_{1-6}$ alkyl and $C_{1-4}$ haloalkyl;

R$^{2q}$ is selected from $C_{1-6}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl ($C_{1-4}$ alkyl), heteroaryl and heteroaryl ($C_{1-4}$ alkyl)- and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

R$^{2r}$R$^{2s}$ taken together with the N form 1-pyrrolidinyl, 1-morpholinyl, 1-piperidinyl or 1-piperazinyl wherein N$^4$ in 1-piperiazinyl is substituted with 0–1 substituents selected from the group R$^{2t}$, CO$_2$R$^{2q}$, COR$^{2q}$ and SO$_2$R$^{2q}$;

R$^{2t}$ is selected from H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl ($C_{1-4}$ alkyl)-, heteroaryl and heteroaryl ($C_{1-4}$ alkyl);

R$^3$ is an aryl or heteroaryl group attached through an unsaturated carbon atom;

aryl is selected from phenyl, naphthyl, indanyl and indenyl, each aryl being substituted with 0–5 substituents independently selected at each occurrence from $C_{1-6}$ alkyl, $C_{3-6}$ cycloalkyl, methylenedioxy, $C_{1-4}$ alkyloxy-$C_{1-4}$ alkyloxy, —OR$^{2m}$, Br, Cl, F, I, $C_{1-4}$ haloalkyl, —CN, —NO$_2$, —SH, —S(O)$_n$R$^{2n}$, —COR$^{2m}$, —CO$_2$R$^{2m}$, —OC(O)R$^{2n}$, NR$^{2g}$COR$^{2m}$, —N(COR$^{2m}$)$_2$, —NR$^{2g}$CONR$^{2o}$R$^{2p}$, —NR$^{2g}$CO$_2$R$^{2h}$, —NR$^{2o}$R$^{2p}$ and CONR$^{2o}$R$^{2p}$;

heteroaryl is selected from the group pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzo-furanyl, 2,3-dihydrobenzothienyl, 2,3-dihydro-benzothienyl-S-oxide, 2,3-dihydrobenzothienyl-s-dioxide, indolinyl, benzoxazolin-2-on-yl, benzodioxolanyl and benzodioxane, each heteroaryl being substituted at 0–4 carbon atoms with a substituent independently selected at each occurrence from $C_{1-6}$ alkyl, $C_{3-6}$ cycloalkyl, Br, F, I, $C_{1-4}$ haloalkyl, —CN, NR$^{2g}$R$^{2h}$, nitro, —OR$^{2m}$, —SH, —S(O)$_n$R$^{2n}$, COR$^{2m}$, —CO$_2$R$^{2m}$, —OC(O)R$^{2n}$, —NR$^{2g}$COR$^{2m}$, —N(COR$^{2m}$)$_2$, and —NR$^{2g}$CONR$^{2o}$R$^{2p}$ and each heteroaryl being substituted at any nitrogen atom with 0–1 substituents selected from the group R$^{2g}$, CO$_2$R$^{3a}$, COR$^{3a}$ and SO$_2$R$^{3a}$ wherein, R$^{3a}$ is selected from the group $C_{1-6}$ alkyl, $C_{1-4}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

R$^4$ is selected from H, Br, Cl, F, I, —CN, $C_{1-6}$ alkyl, $C_{2-6}$ alkenyl, $C_{2-6}$ alkynyl, $C_{3-8}$ cycloalkyl, $C_{1-6}$ alkyloxy, $C_{1-6}$ alkylthio, $C_{1-6}$ alkylsulfinyl, $C_{1-6}$ alkylsulfonyl, amino, $C_{1-4}$ alkylamino, ($C_{1-4}$ alkyl)$_2$ amino and phenyl, each phenyl is substituted with 0–3 groups selected from the group consisting of $C_{1-7}$ alkyl, $C_{3-8}$ cycloalkyl, Br, Cl, F, I, —C(O)H, $C_{1-4}$ haloalkyl, nitro, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, $C_{1-6}$ alkylamino and ($C_{1-4}$ alkyl)$_2$ amino and wherein R$^4$ non-phenyl groups may be substituted with 0–5 substituents selected from OH, halogen, —C(O)H, —OC$_{1-6}$-alkyl, $C_{1-6}$ haloalkyl, $C_{1-6}$ alkyl, $C_{3-7}$ c-alkyl, and $C_{1-6}$ alkyl(OH)$_n$CO$_2$R, wherein R is H or $C_{1-6}$ alkyl, or $C_{1-6}$ alkyl(OH)$_n$, wherein n is 0–3;

R$^6$, R$^{6a}$ and R$^7$ are independently selected from: H, $C_{1-10}$ alkyl, $C_{3-10}$ cycloalkyl, $C_{3-10}$ alkenyl, $C_{3-10}$ alkynyl, $C_{1-10}$ haloalkyl, $C_{2-8}$ alkoxyalkyl, $C_{4-12}$ cycloalkylalkyl, $C_{5-10}$ cycloalkenyl, and $C_{6-14}$ cycloalkenylalkyl; and R$^6$, R$^{6a}$ and R$^7$ are substituted with 0–6 substituents independently selected from halogen, $C_{1-4}$ alkyl, $C_{3-8}$ cycloalkyl, $C_{1-6}$ alkyloxy, and $C_{1-4}$ haloalkyl.

3. A compound according to claim 1 wherein

R$^1$ is selected from $C_{1-6}$ alkyl, $C_{3-6}$ cycloalkyl, $C_{1-6}$ alkoxy, $C_{1-6}$ alkylthio, and —XR$^{1c}$ wherein R$^1$ is substituted with 0–6 substituents selected from halogen, $C_{1-4}$ alkyl and $C_{1-4}$ haloalkyl;

R$^2$ is selected from $C_{1-10}$ alkyl, $C_{2-10}$ alkenyl, $C_{2-10}$ alkynyl, $C_{3-8}$ cycloalkyl, $C_{3-6}$ cycloalkyl $C_{1-6}$ alkyl, and —NR$^{2c}$R$^{2d}$ wherein R$^2$ is unsubstituted or substituted with 1–3 substituents independently selected from the group R$^{2i}$, R$^{2j}$, R$^{2k}$, $C_{1-6}$ alkyl, $C_{2-8}$ alkenyl, $C_{2-8}$ alkynyl, Br, Cl, F, I, $C_{1-4}$ haloalkyl, —$OR^{2g}$, —$NR^{2g}R^{2h}$, —$C_{1-6}$ alkyl-$OR^{2g}$, and $C_{3-8}$ cycloalkyl which is substituted with 0–1 $R^{2i}$ and in which 0–1 carbons of $C_{4-8}$ cycloalkyl is replaced by —O—.

4. A compound according to claims 1, wherein $R^3$ is an aryl group selected from phenyl and substituted versions thereof or a heteroaryl group selected from pyridyl and substituted versions thereof.

5. A compound according to claim 4 wherein $R^3$ is substituted with 0–4 substituents independently selected from halogen, $C_{1-4}$ alkyloxy, $C_{1-6}$ alkyl and NR'R" wherein R' and R" are independently selected from H and $C_{1-6}$ alkyl.

6. A compound according to claim 1 wherein $R^2$ is selected from 3-pentyl, $NEt_2$, butyl, $NHCH(CH_2OMe)_2$, $NHCH(CH_2OEt)_2$, $NHCH(Et)CH_2OMe$, NH-3-heptyl, NH-3-pentyl, NH-2-butyl, NH-3-hexyl, $NHCH(CH_2Ph)CH_2OMe$, $NHCH(Et)CH_2CH_2OMe$, NH-cyclobutyl, NH-cyclopentyl, NEtPr, NEtBu, NMePr, NMePh, $Npr_2$, $NPr(CH_2$-c-$C_3H_5)$, $N(CH_2CH_2OMe)_2$, morpholino, $N(CH_2Ph)CH_2CH_2OMe$, $N(Me)CH_2CH_2OMe$, $N(Et)CH_2CH_2OMe$, $N(CH_2$-c-$C_3H_5)CH_2CH_2OMe$, $N(CH_2$-c-$C_3H_5)Pr$, $N(CH_2$-c-$C_3H_5)Et$, OEt, $OCH(Et)CH_2OMe$, $OCH(Et)CH_2CH_2OMe$, $OCH(Me)CH_2CH_2OMe$, O-3-pentyl, O-2-pentyl, S-3-pentyl, S-2-pentyl, SEt, S(O)Et, $SO_2Et$, S-3-pentyl, S(O)-3-pentyl, $SO_2$-3-pentyl, S-2-pentyl, S(O)-2-pentyl, $SO_2$-2-pentyl, $CH(CO_2Et)_2$, $C(Et)(CO_2Et)_2$, $CH(Et)CH_2OH$, $CH(Et)CH_2OMe$, $CH(Et)CH_2CH_2OMe$, $CONMe_2$, $COCH_3$, COEt, COPr, CO-2-pentyl, CO-3-pentyl, $CH(OH)CH_3$, $C(OH)Me_2$, C(OH)Ph-3-pyridyl, $CH(OMe)CH_3$, CH(OMe)Et, CH(OMe)Pr, $CH(OEt)CH_3$, $CH(OPr)CH_3$, 2-pentyl, 2-butyl, cyclobutyl, cyclopentyl, CH(Me)cyclobutyl, CH(OMe)cyclobutyl, CH(OH)cyclobutyl, CH(Me)cyclopropyl, CH(OMe)cyclopropyl, CH(OH)cyclopropyl, CH(Et)cyclobutyl, CH(Et)cyclopropyl, CH(OMe)cyclobutyl, CH(OMe)cyclopropyl, CH(OEt)cyclobutyl, CH(OEt)cyclopropyl, $CH(Me)CH_2$-cyclobutyl, $CH(OMe)CH_2$-cyclobutyl, $CH(OH)CH_2$-cyclobutyl, $CH(Me)CH_2$-cyclopropyl, $CH(OMe)CH_2$-cyclopropyl, $CH(OH)CH_2$-cyclopropyl, $CH(Et)CH_2$-cyclobutyl, $CH(Et)CH_2$-cyclopropyl, $CH(OMe)CH_2$-cyclobutyl, $CH(OMe)CH_2$-cyclopropyl, $CH(OEt)CH_2$-cyclobutyl, $CH(OEt)CH_2$-cyclopropyl, $CH(CH_2OMe)$cyclobutyl, $CH(CH_2OMe)$cyclopropyl, $CH(CH_2OEt)$cyclobutyl, $CH(CH_2OEt)$cyclopropyl, $CH(cyclobutyl)_2$, $CH(cyclopropyl)_2$, $CH(Et)CH_2CONMe_2$, $CH(Et)CH_2CH_2NMe_2$, $CH(CH_2OMe)Me$, $CH(CH_2OMe)Et$, $CH(CH_2OMe)Pr$, $CH(CH_2OEt)Me$, $CH(CH_2OEt)Et$, $CH(CH_2OEt)Pr$, $CH(CH_2C\equiv CMe)Et$, and $CH(CH_2C\equiv CMe)Et$.

7. A method of antagonizing a CRF-1 receptor in mammals including humans wherein binding to the receptor causes and ultimately results in the treatment of affective disorder, anxiety, depression, irritable bowel syndrome, stroke, comprising administering to the mammal a therapeutically effective amount of a compound according to claims 1 to 6.

8. A pharmaceutical composition comprising a compound according to any one of claims 1 to 6 and a pharmaceutically acceptable carrier.

* * * * *